United States Patent
Kirschhoffer et al.

(10) Patent No.: US 9,428,787 B2
(45) Date of Patent: Aug. 30, 2016

(54) APPARATUS AND METHOD FOR PROCESSING A SAMPLE

(71) Applicant: 3M INNOVATIVE PROPERTIES COMPANY, St. Paul, MN (US)

(72) Inventors: Jon A. Kirschhoffer, Stillwater, MN (US); Andrew H. Tilstra, Shoreview, MN (US); Wensheng Xia, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/405,012

(22) PCT Filed: May 24, 2013

(86) PCT No.: PCT/US2013/042560
§ 371 (c)(1),
(2) Date: Dec. 2, 2014

(87) PCT Pub. No.: WO2013/184397
PCT Pub. Date: Dec. 12, 2013

(65) Prior Publication Data
US 2015/0118705 A1    Apr. 30, 2015

Related U.S. Application Data

(60) Provisional application No. 61/655,613, filed on Jun. 5, 2012.

(51) Int. Cl.
*B01L 3/00* (2006.01)
*C12Q 1/04* (2006.01)
*C12Q 1/24* (2006.01)

(52) U.S. Cl.
CPC ............ *C12Q 1/04* (2013.01); *B01L 3/5023* (2013.01); *C12Q 1/24* (2013.01); *B01L 2200/026* (2013.01);
(Continued)

(58) Field of Classification Search
CPC .............. B01L 2200/026; B01L 2200/04; B01L 2200/0609; B01L 2200/0825; B01L 2200/0877; B01L 3/5023
See application file for complete search history.

(56) References Cited

U.S. PATENT DOCUMENTS

2002/0001854 A1  1/2002 Lee
2002/0125197 A1  9/2002 Hager et al.
(Continued)

FOREIGN PATENT DOCUMENTS

DE  10 2007 014 729  9/2008
EP  1 588 764  10/2005
(Continued)

OTHER PUBLICATIONS

Berry, E.D. et al.; "Hydroxyapatite Adherence as a Means to Concentrate Bacteria"; Applied and Environmental Microbiology; vol. 63, No. 10; 1997; pp. 4069-4074.
(Continued)

*Primary Examiner* — Paul Hyun

(57) ABSTRACT

An apparatus and an assembly for processing a sample are provided. The apparatus comprises a plurality of spaced-apart reservoirs, a plurality of channels, and a plurality of outlets, each outlet comprising an effluent discharge opening. The apparatus forms a plurality of flow paths, each flow path comprising a reservoir, a channel, and an outlet. An analyte capture element can be slideably engaged in a channel in a position where it is in fluid communication with the flow path. The apparatus with the analyte capture element disposed in the flow path can be used to process a liquid sample. A method of detecting an analyte in the liquid sample is also provided.

20 Claims, 10 Drawing Sheets

(52) U.S. Cl.
CPC ..... *B01L 2200/04* (2013.01); *B01L 2300/0609* (2013.01); *B01L 2300/0825* (2013.01); *B01L 2300/0877* (2013.01)

(56) References Cited

U.S. PATENT DOCUMENTS

| | | |
|---|---|---|
| 2003/0080454 A1 | 5/2003 | Moll et al. |
| 2003/0091989 A1 | 5/2003 | Davis et al. |
| 2004/0158188 A1 | 8/2004 | Kauffmann et al. |
| 2005/0103703 A1 | 5/2005 | Young et al. |
| 2007/0298451 A1 | 12/2007 | Ribault et al. |
| 2008/0011062 A1* | 1/2008 | Sarofim ............... B01L 3/5025 73/64.56 |
| 2008/0299621 A1 | 12/2008 | Tatnell et al. |
| 2010/0209961 A1 | 8/2010 | Kshirsagar et al. |

FOREIGN PATENT DOCUMENTS

| | | |
|---|---|---|
| EP | 1 813 949 | 8/2007 |
| EP | 1 953 552 | 8/2008 |
| WO | WO 93/11221 | 6/1993 |
| WO | WO 96/41810 | 12/1996 |
| WO | WO 97/08306 | 3/1997 |
| WO | WO 2008/006617 | 1/2008 |
| WO | WO 2008/134472 | 11/2008 |
| WO | WO 2009/046191 | 4/2009 |
| WO | WO 2010/075116 | 7/2010 |
| WO | WO 2010/078234 | 7/2010 |
| WO | WO 2012/066032 | 5/2012 |
| WO | WO 2012/092123 | 7/2012 |
| WO | WO 2012/122088 | 9/2012 |
| WO | WO 2013/184398 | 12/2013 |

OTHER PUBLICATIONS

Oster, J. et al.; "Polyvinyl-alcohol-based magnetic beads for rapid and efficient separation of specific or unspecific nucleic acid sequences"; Journal of Magnetism and Magnetic Materials; vol. 225; 2001; pp. 145-150.

* cited by examiner

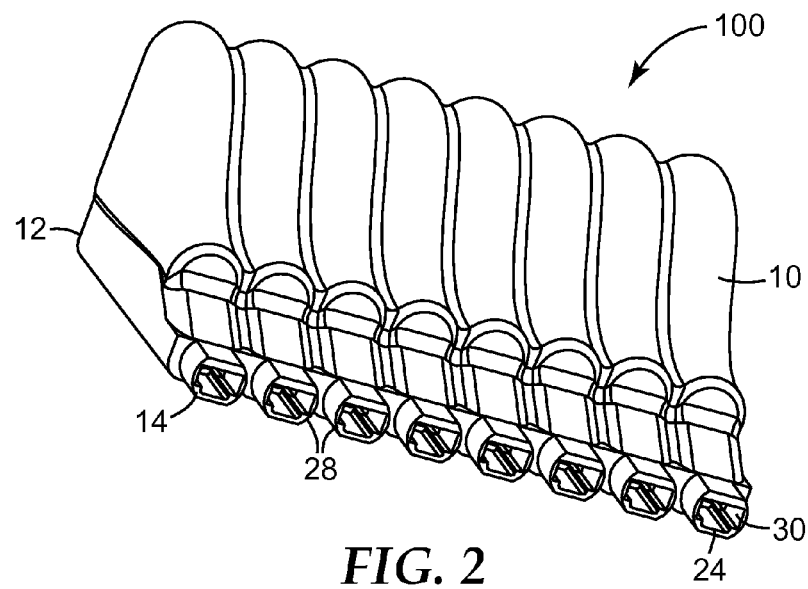
FIG. 2
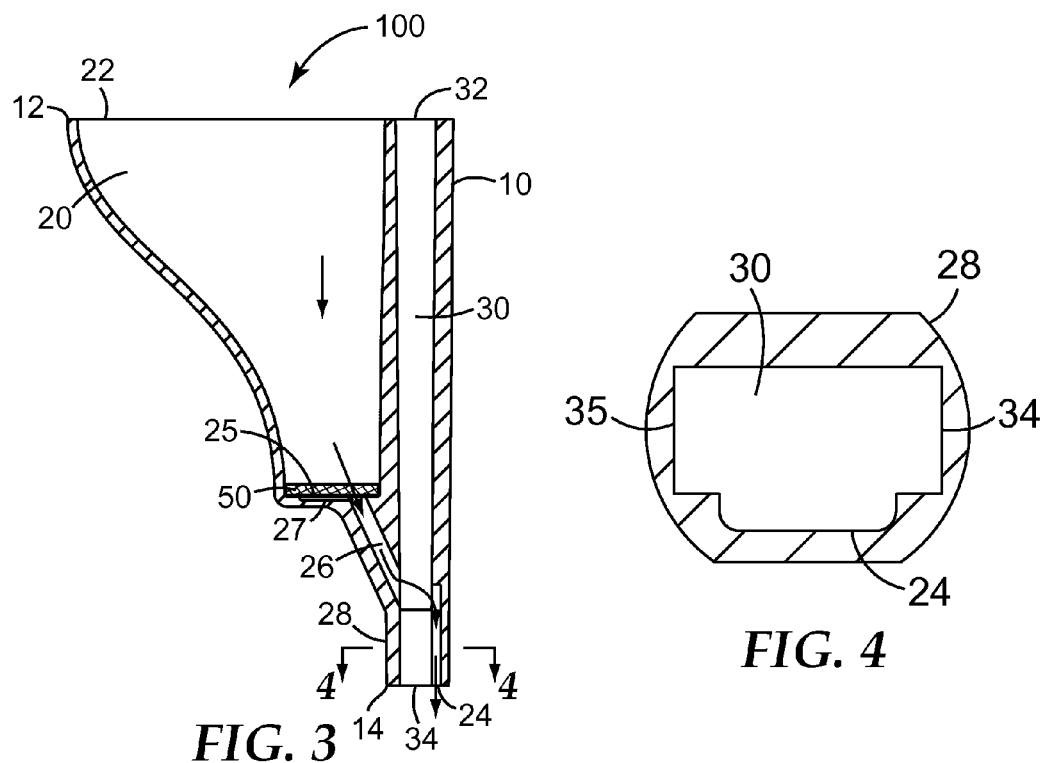
FIG. 3
FIG. 4

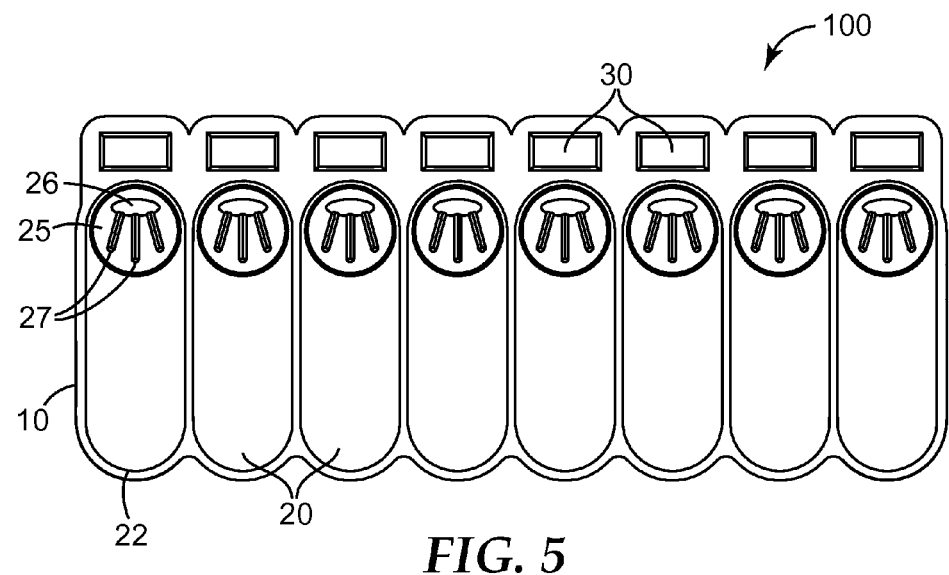
*FIG. 5*
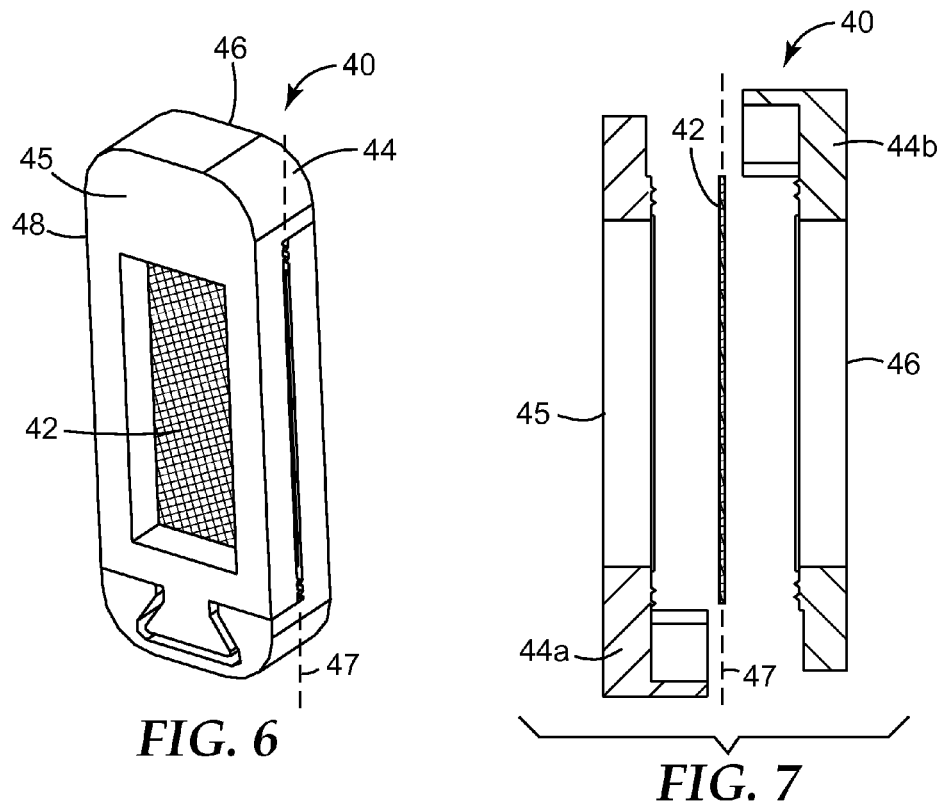
*FIG. 6*　　　*FIG. 7*

APPARATUS AND METHOD FOR PROCESSING A SAMPLE

CROSS REFERENCE TO RELATED APPLICATIONS

This application is a national stage filing under 35 U.S.C. 371 of PCT/US2013/042560, filed May 24, 2013, which claims the benefit of U.S. Provisional Patent Application No. 61/655,613, filed Jun. 5, 2012, which is incorporated herein by reference in its entirety.

BACKGROUND

Many types of samples (e.g., clinical, environmental, food, and beverage samples) are routinely tested for the presence or absence of microorganisms. In particular many samples are tested for the presence of pathogenic microorganisms. Often, the samples require various types of pre-treatment (i.e., processing prior to a detection step) in order to increase the number of target microorganisms, decrease the number of non-target microorganisms, concentrate the microorganisms, and/or reduce the quantity of potentially-interfering material in the sample. The pre-treatment steps may be laborious and can take several hours to several days to complete. A variety of materials and devices have been developed to reduce the number of steps and the time that it takes to complete the pre-treatment of samples.

Processing a plurality of samples simultaneously can be difficult because of the lack of simple, efficient devices for the procedure. There remains a need for simple, rapid methods to prepare one or more samples for the detection of microorganisms.

SUMMARY

In general, the invention is directed to the detection of a microorganism in a sample. In particular, the present disclosure provides an apparatus and a corresponding method of use for processing a sample to detect the presence or absence of a target analyte. In some embodiments, the analyte may be associated with a microorganism. Advantageously, the apparatus is configured to releasably hold an analyte capture element in a chamber. After contacting a liquid sample with the analyte capture element, the capture element can be ejected from the chamber and processed to detect the presence or absence of the target analyte.

In one aspect, the present disclosure provides an apparatus for processing a sample. The apparatus can comprise a body having a first end and a second end opposite the first end. The body can comprise a plurality of spaced-apart reservoirs in a linear array, each reservoir comprising a sample-receiving opening; a plurality of spaced-apart effluent discharge openings, each effluent discharge opening in fluid communication with one of the plurality of sample-receiving openings via a flow path; a plurality of channels, each channel intersecting one of the flow paths; and a plurality of spaced-apart outlets extending from the body, each of the outlets comprising one of the second channel openings. Each channel can comprise a second channel opening proximate the second end. Each channel can be dimensioned to receive an analyte capture element. In any embodiment, each of the outlets further can comprise one of the effluent discharge openings. In any of the above embodiments, the effluent discharge opening and the second channel opening can define a common opening.

In any of the above embodiments, the apparatus further can comprise an analyte capture element slideably engaged in a channel at a location that is in fluid communication with the flow path that intersects the channel in which the analyte capture element is disposed. In any embodiment, the analyte capture element can comprise a holder with a capture medium attached thereto.

In any of the above embodiments, the apparatus further can comprise a first retention structure disposed in a channel, wherein the first retention structure is configured to position an analyte capture element, if present, at a location in the channel where the analyte capture element is in fluid communication with the flow path that intersects the channel. In any embodiment, the apparatus further can comprise a second retention structure disposed in the channel, wherein the first and second retention structures are configured to releasably hold the analyte capture element, if present, at a location where the analyte capture element is in fluid communication with the flow path. In any of the embodiments, the apparatus can be configured such that substantially all liquid passing through the flow path from the sample-receiving opening to the effluent discharge opening passes through the analyte capture element. In some embodiments, the holder can comprise a first face, a second face opposite the first face, and a longitudinal plane between the first face and the second face; wherein the capture medium is disposed in the holder substantially along the longitudinal plane. In some embodiments, the holder can comprise a first face, a second face opposite the first face; wherein the capture medium is disposed on the holder substantially along the first or second face. In some embodiments, the holder can comprise a first face, a second face opposite the first face, and a longitudinal plane between the first face and the second face; wherein the capture medium is disposed in the holder in a plane that is oriented from a portion of the first face to a portion of the second face.

In any of the above embodiments, the channel can extend from the second channel opening to a first channel opening. In some embodiments, the first channel opening can be disposed at the first end. In any of the above embodiments, the apparatus further can comprise an analyte capture element discharger comprising a post, wherein a portion of the post is disposed in the channel, wherein the discharger is configured to move through the channel and to urge an analyte capture element, if present in the channel, out of the second channel opening. In any of the above embodiments, the sample-receiving opening of each of the plurality of chambers can be covered with a pierceable seal. In any of the above embodiments, the apparatus further can comprise a prefilter disposed in a flow path between the sample-receiving opening of the flow path and the channel that intersects the flow path. In any of the above embodiments, each outlet of the plurality of outlets can be shaped, dimensioned, and spaced apart such that the plurality of outlets can be received into a linear array of two or more tubes.

In another aspect, the present disclosure provides an assembly. The assembly can comprise the apparatus of any one of the above embodiments and a waste receptacle operably coupled thereto. The apparatus can comprise a first reservoir having a first sample-receiving opening and a first outlet having a first effluent discharge opening and a second reservoir adjacent the first reservoir, the second reservoir having a second sample-receiving opening and a second outlet having a second effluent discharge opening. The waste receptacle can comprise a plurality of spaced-apart chambers, wherein the plurality of spaced-apart chambers. The plurality of spaced-apart chambers can comprise a first chamber having a first interior volume and a first drain and a second chamber adjacent the first chamber, the second chamber having a second interior volume and a second drain. The assembly further can comprise an analyte capture element slideably engaged in one of the channels. When the apparatus and the waste receptacle are operably coupled, a first liquid flow path can extend from the first sample-receiving opening to the first drain, and a second liquid flow path can extend from the second sample-receiving opening to the second drain. A first shortest distance between the first effluent discharge opening and the second effluent discharge opening can be shorter than a second shortest distance between the first drain and the second drain.

In any of the above embodiments of the assembly, when the apparatus and the waste receptacle are operably coupled, at least a portion of the first outlet can be disposed in the first interior volume and at least a portion of the second outlet can be disposed in the second interior volume. In any of the above embodiments of the assembly, each of the plurality of chambers can comprise a substantially planar floor, wherein the floor comprises the drain. In some embodiments, the floor further can comprise a trough extending along a portion of the floor to the drain. In any of the above embodiments of the assembly, the waste receptacle is adapted to be coupled to a source of negative pressure.

In yet another aspect, the present disclosure provides a method of detecting a presence or an absence of an analyte in a sample. The method can comprise providing a liquid sample and any of the above embodiments of the apparatus or assembly, wherein at least one analyte capture element is movably engaged a channel. The method further can comprise contacting the liquid sample with the at least one analyte capture element, ejecting the at least one analyte capture element from the channel, and detecting a presence or an absence an analyte retained from the sample by the analyte capture element. In any embodiment of the method, contacting the liquid sample with the at least one analyte capture element can comprise loading the sample into a reservoir that is in fluidic communication with the at least one analyte capture element. In any of the above embodiments, the method further can comprise the step of operably connecting the apparatus or the assembly to a source of negative pressure. In some embodiments, ejecting the at least one analyte capture element can comprise sliding the capture element out of an opening at the second end of the apparatus. In any of the above embodiments of the method, ejecting the at least one analyte capture element from the channel comprises moving a discharge element through a portion of the channel to eject the analyte capture element from the channel.

In any of the above embodiments of the method, the at least one capture element can comprise a porous medium, wherein contacting the liquid sample with the at least one capture element comprises passing the liquid sample through the porous medium. In any of the above embodiments, the method further can comprise the step of processing the at least one analyte capture element and/or sample material associated therewith to permeabilize a cell. In any of the above embodiments of the method, detecting a presence or an absence an analyte retained from the sample can comprise detecting a nucleotide, a nucleic acid, an enzyme, an antigen or a combination of any two or more of the foregoing analytes. In any of the above embodiments, the method further can comprise the step of coupling at least one outlet to a container, wherein ejecting the at least one analyte capture element from the channel comprises ejecting the analyte capture element into the container.

In yet another aspect, the present disclosure provides a kit. The kit can comprise an apparatus comprising a body having a first end and a second end opposite the first end. The body can comprise a plurality of spaced-apart reservoirs in a linear array, each reservoir comprising a sample-receiving opening proximate the first end; a plurality of spaced-apart effluent discharge openings, each effluent discharge opening in fluid communication with one of the plurality of sample-receiving openings via a flow path; a plurality of channels, each channel intersecting one of the flow paths; and a plurality of spaced-apart outlets extending from the body, each of the outlets comprising one of the second channel openings. Each channel can comprise a second channel opening proximate the second end. Each channel can be dimensioned to receive an analyte capture element.

In any of the above embodiments, the kit further can comprise a waste receptacle. The waste receptacle can comprise a plurality of spaced-apart chambers, each chamber having an outlet-receiving opening, an interior volume, and a drain. The plurality of spaced-apart chambers can comprise a first chamber having a first interior volume and a first drain and a second chamber adjacent the first chamber, the second chamber having a second interior volume and a second drain. When the apparatus and the waste receptacle are operably coupled, at least a portion of the first outlet is disposed in the first interior volume forming a first flow path extending from the first sample-receiving opening to the first drain and at least a portion of the second outlet is disposed in the second interior volume forming a second flow path extending from the second sample-receiving opening to the second drain, wherein a first shortest distance between a first outlet opening and a second outlet opening is shorter than a second shortest distance between the first drain and the second drain.

In any of the above embodiments, the kit further can comprise an analyte capture element that is configured to be disposed in one of the plurality of channels such that liquid passing through one of the flow paths from the first end to the second end contacts the analyte capture element. In any of the above embodiments, the kit further can comprise at least one analyte capture element discharger. In any of the above embodiments, the kit further can comprise a reagent. In some embodiments, the reagent can comprise a cell lysis agent or a detection agent.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a reservoir can be interpreted to mean "one or more" reservoirs.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF THE DRAWINGS

FIG. 2 is a bottom perspective view of the apparatus of FIG. 1.

FIG. 3 is a cross-sectional view of the apparatus of FIG. 1, showing a liquid flow path extending from the first end to the second end.

FIG. 4 is cross-sectional view of the outlet shown in FIG. 3.

FIG. 5 is a top view of the apparatus of FIG. 1 without the optional cover.

FIG. 6 is a perspective view of one embodiment of an analyte capture element according to the present disclosure.

FIG. 7 is an exploded side view of the analyte capture element of FIG. 6.

DETAILED DESCRIPTION

Figure 1:
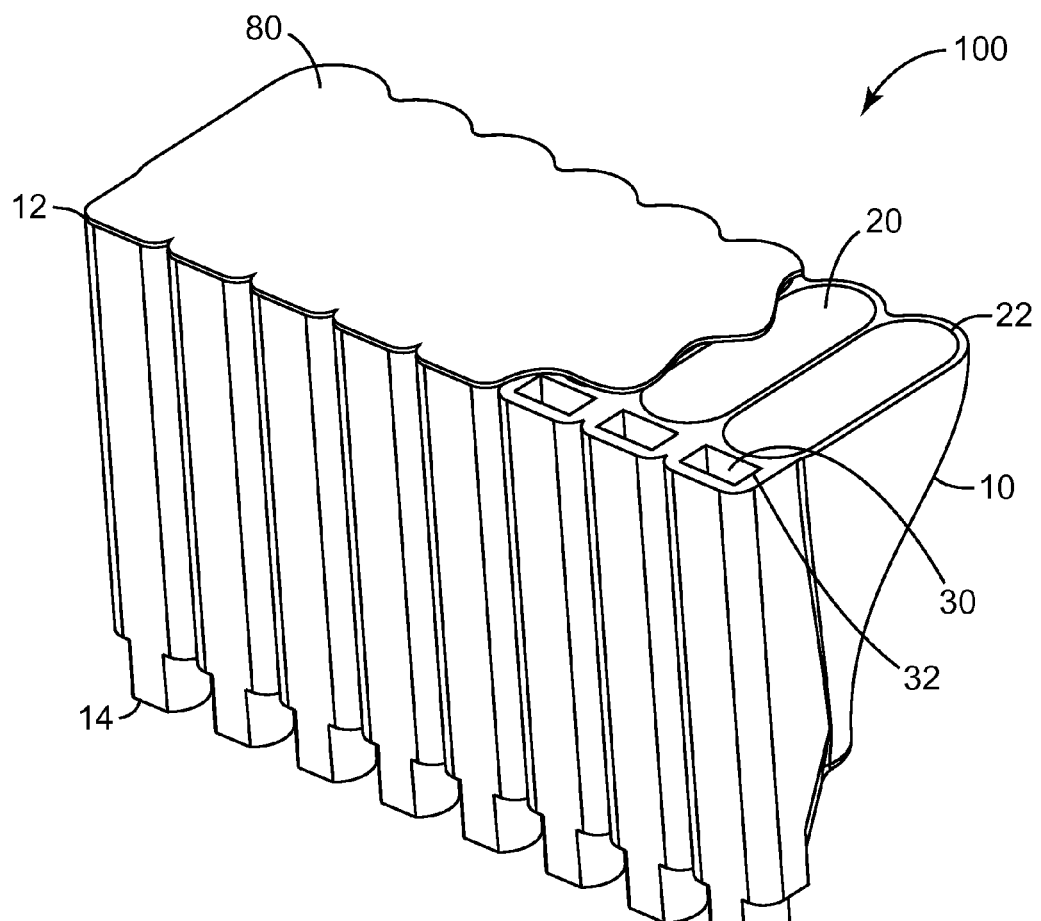
FIG. 1 is an upper perspective view, partially in section, of one embodiment of an apparatus for processing a sample according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a process of preparing a sample to detect the presence or absence of an analyte. In particular, the present disclosure provides an apparatus and a method to facilitate a processes of concentrating the analyte by capturing the analyte on and/or in an analyte capture element and, subsequently, detecting the presence or absence of any analyte retained from the sample by the analyte capture element. In addition, a single step can be used to transfer the resulting retained analyte from the apparatus to a separate container for further processing and/or detection of the analyte. The analyte captured using this apparatus and method is relatively concentrated, relatively free of impurities, and is suitable for use in a variety of detection methods (e.g., immunodetection methods and nucleic acid detection methods).

The present disclosure includes methods and an apparatus for processing a plurality of samples. The plurality of samples may comprise samples from independent sources. Alternatively or additionally, the samples may comprise samples obtained from a single source (e.g., replicate sample; samples removed at different time points; replicate samples that were subjected to different treatments). The inventive methods relate to the detection of an analyte in a sample. In any embodiment, the analyte can be a biological analyte such as, for example, a biological analyte that indicates the presence of a microorganism in the sample.

The sample can be any sample that may comprise an analyte. The analyte may comprise a chemical analyte and/or a biological analyte. Nonlimiting examples of suitable samples include suspensions or cultures of cells (e.g., mammalian cells, insect cells, yeast cells, filamentous fungi, bacterial cells), environmental samples (e.g., surface swabs), food (e.g., raw materials, in-process samples, and finished-product samples), beverages, clinical samples (e.g., blood, urine, sputum, tissue, mucous, feces, wound exudate, pus), and water (e.g., surface water, potable water, process water).

Non-limiting examples of suitable biological analytes include nucleic acids (e.g., a polynucleotide associated with a particular type of cell or microorganism) or detectable antigens (e.g., proteins, oligopeptides, enzymes, endotoxin, cell membrane components, and cell wall components). Analytical procedures to detect the biological analytes are known in the art. Preferred biological analytes to be detected include nucleic acids that are capable of being amplified in a reaction (e.g., polymerase chain reaction (PCR)), for example.

Besides fluid samples, other test samples may include liquids as well as solid(s) dissolved or suspended in a liquid medium. Samples of interest may include process streams, water, soil, plants or other vegetation, air, surfaces (e.g., contaminated surfaces), and the like. Samples can also include cultured cells. Samples can also include samples on or in a device comprising cells, spores, or enzymes (e.g., a biological indicator device).

Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method. Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

Suitable samples also include cell-suspension media (e.g., culture broth, semi-solid cell culture media, and tissue culture media, filtrate) that contain cells or previously contained cells. Suitable samples also include cell lysates. Cell lysates may be produced by chemical means (e.g., detergents, enzymes), mechanical means (sonic vibration, homogenization, French Press), or by other cell lytic means known in the art.

Microorganisms (e.g., bacteria, fungi, viruses) are a source of detectable analytes. Microorganisms can be analyzed in a test sample that may be derived from a variety of sources, as described herein. Microorganisms of particular interest include prokaryotic and eukaryotic organisms, particularly Gram positive bacteria, Gram negative bacteria, fungi, protozoa, mycoplasma, yeast, viruses, and even lipid-enveloped viruses. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus* anthracia, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V. parahemolyticus*, *Salmonella cholerasuis*, *S. typhi*, *S. typhimurium*, *Candida albicans*, *C. glabrata*, *C. krusei*, *Enterobacter sakazakii*, *E. coli* O157 and multiple drug resistant Gram negative rods (MDR).

Gram positive and Gram negative bacteria are of particular interest. Of even more interest are Gram positive bacteria, such as *Staphylococcus aureus*. Also, of particular interest are antibiotic resistant microbes including MRSA, VRSA, VISA, VRE, and MDR.

In order to facilitate a complete understanding, the remainder of the detailed description describes apparatuses and assemblies for processing a sample by reference to the drawings, wherein like elements among the embodiments are referenced with like numerals throughout the following description. Turning to the drawings, FIGS. 1 and 2 show top and bottom perspective views, respectively, of one embodiment of an apparatus 100 for processing a sample.

The apparatus 100 comprises a body 10. The body 10 has a first end 12 and a second end 14 opposite the first end 12. The body 10 comprises a plurality of spaced-apart reservoirs 20. The reservoirs 20 may form an array such as a linear array of reservoirs 20, for example, as shown in FIG. 1. Each reservoir 20 in the plurality of reservoirs comprises a sample-receiving opening 22 at the first end 12 and an effluent discharge opening 24 at the second end 14. The body 10 also comprises a plurality of channels 30, each channel having a first channel opening 32 at the first end 12 of the body 10. Each of the plurality of channels 30 is positioned proximate one of the plurality of reservoirs 20 and substantially aligned with a flow path (not shown) that passes through a reservoir 20 and extends from the first end 12 to the second end 14 of the body 10. The second end 14 of the body 10 comprises a plurality of spaced-apart outlets 28. The outlets 28 may be shaped and dimensioned to be inserted into a predefined container (e.g., a reaction tube, a well of a 96-well plate).

In a preferred embodiment, the plurality of outlets 28 is appropriately dimensioned and spaced-apart such that the plurality of outlets 28 can be inserted (e.g., simultaneously) into a linear array of two or more tubes (e.g., a plurality of reaction tubes such as a linear array of 1.1 mL minitubes, part number MTS-8-C-R, available from Axygen, Inc. Union City, Calif., for example). In some embodiments, the tubes of the linear array may have a center-to-center distance of about 9 mm or less. In some embodiments, the tubes of the linear array may have a center-to-center distance of about 2 mm to about 20 mm.

The volume of the reservoirs 20 can be configured according to the typical size of the sample to be tested. In some embodiments, the volume of the reservoir 20 is at least about one milliliter. In some embodiments, the volume of the reservoir 20 is at least about five milliliters. In some embodiments, the volume of the reservoir 20 is at least about ten milliliters. In some embodiments, the volume of the reservoir 20 is at least about twenty-five milliliters. In some embodiments, the volume of the reservoir 20 is at least about one hundred milliliters. Larger volumes of liquid sample can be tested by passing two or more aliquots of the sample sequentially through the same reservoir 20.

Also shown in FIG. 1 is an optional cover 80. The cover 80 protects each reservoir 20 from the entry of undesirably material. In some embodiments, the cover 80 may comprise a thin sheet (e.g., a plastic film or coated paper). Preferably, the cover 80 is attached (e.g., removably attached) to the body 10 via a heat bond or a pressure-sensitive adhesive, for example. In certain preferred embodiments, the cover 80 may comprise a pierceable film (e.g., pierceable by a pipette tip) and or the cover may be optically translucent or transparent, thereby permitting visualization of contents present in the reservoirs 20.

FIG. 3 is a cross-sectional view of the body 10 of the apparatus 100 of FIG. 1. The reservoir 20 has an opening 22 through which a sample (e.g., a liquid sample or a suspension of solid material in a liquid, not shown) is deposited into the reservoir 20. Also shown in FIG. 3 are a channel 30 and an effluent discharge opening 24, which are both in fluid communication with the reservoir 20 via a conduit 26. Thus, the apparatus 100 of the present disclosure defines a liquid flow path (e.g., a liquid flow path), shown by the arrows, extending from the sample-receiving opening 22 at the first end 12 of the body 10 to the effluent discharge opening 24 at the second end 14 of the body 10. In the illustrated embodiment of FIGS. 1-3, the second channel opening 34 and effluent discharge opening 24 form a common opening 35 (shown in FIG. 4) in an outlet 28 at the second end 14 of the body. In an alternative embodiment discussed below, each of the second channel opening and effluent discharge opening comprise separate openings proximate the second end of the body.

Optionally, the apparatus 100 further may comprise a prefilter 50. The prefilter 50 substantially remove particulate materials that are larger than a bacterium (e.g., ≥5 mm diameter) serves to trap and substantially remove particulate materials that are larger than a bacterium (e.g., ≥5 µm diameter) that may be present in a liquid sample passing there through. The reservoir 20 is configured such that a liquid sample moving through the reservoir 20 from the sample-receiving opening 22 to the effluent discharge opening 24 substantially passes through the prefilter 50. The prefilter 50 can be supported by the optional base 25. In some embodiments, the prefilter 50 optionally may be coupled (e.g., via an adhesive or other secural means, not shown) to the base 25. Also shown in FIG. 3 is a gutter 27 in the base 25. The gutter 27 is described in further detail below.

The prefilter 50 can be constructed from a variety of materials known in the art (e.g., nonwoven materials comprising nylon, polypropylene, glass, or cellulose acetate fibers, for example; or perforated films such as polycarbonate films, for example). In any embodiment, the prefilter 50 may comprise a single layer of material. In some embodiments, the prefilter 50 may comprise a plurality of layers (not shown). A layer of a prefilter comprising a plurality of layers may comprise a particulate material to facilitate the removal of certain non-analyte materials (e.g., fats, minerals) from the sample.

The prefilter 50, or a layer thereof, may comprise a membrane filter or a relatively coarse nonwoven depth filter (approximately 1 mm thick) made from polyethylene fibers. The prefilter 50 or layer thereof, may have a nominal porosity of approximately 20-50 µm and can function to prevent the passage of large particles into other layers of the prefilter, if present. The prefilter 50, or layer thereof, may comprise a wet-laid fibrous scaffold (approximately 0.2-1 mm thick), optionally containing particulate material that removes a one or more specific non-analyte materials. A non-limiting example of a material that may be used in a prefilter 50 individually or in any combination with other materials is a polypropylene felt filter (part number NB005PPS2R, 5 µm nominal porosity, available from CUNO 3M, Meriden, Conn.). Other known layers (not shown) and/or materials may be used in prefilter 50, with each layer functioning to reduce the amount of non-analyte material in the liquid sample as it passes through the prefilter 50.

Referring back to the drawings, FIG. 5 shows a top view of the apparatus of FIG. 1. The body 10 comprises a plurality of reservoirs 20 and a plurality of channels 30 arranged in side-by-side linear arrays. Each reservoir 20 comprises a sample-receiving opening 22 and a conduit 26, which form part of the liquid flow path (designated by arrows) shown in FIG. 3. Also shown is the base 25 on which a prefilter (not shown) can be disposed. Optionally, the base 25 further can comprise one or more gutters 27, which may comprise, for example, depressions that extend along the base 25 away from the conduit 26 in one or more directions. In use, the gutters 27 guide liquid along the base toward the conduit 26.

In any embodiment, the apparatus of the present disclosure further can comprise an analyte capture element. FIG. 6 shows a perspective view of one embodiment of an analyte capture element 40 according to the present disclosure. FIG. 7 shows an exploded cross-sectional side view of the analyte capture element 40 of FIG. 6. The analyte capture element 40 comprises a capture medium 42 and, optionally, a holder 44. In the illustrated embodiment of FIG. 6, the holder 44 is a frame-like structure comprising two portions (44a and 44b, respectively) that are press-fit together and, when joined, securely hold the capture medium 42. The holder 44 has a first face 45, a second face 46, and a longitudinal plane 47 between the first face 45 and the second face 46. In some embodiments (e.g., the illustrated embodiment of FIGS. 6 and 7), the capture medium 42 is disposed in the holder 44 substantially along the longitudinal plane 47. In an alternative embodiment discussed below, the capture medium 42 can be attached (e.g., detachably attached) to the holder 44 via an adhesive (e.g., a pressure sensitive adhesive), an ultrasonic weld, a heat bond, and/or an insert mold at any point on the holder 44. In some embodiments (shown in FIG. 11 and described below), the capture medium 42 can be disposed on the holder 44 substantially along the first 45 or second face 46. For example, the capture medium 42 can be attached along an edge 48 of the first face 45 of the holder 44. In one embodiment, not shown, the capture medium can be disposed in the holder in a plane that is oriented from a portion of the first face to a portion of the second face (e.g., diagonal to the longitudinal plane shown in FIG. 7. The holder 44 may be fabricated from a variety of materials using methods that are well known in the art. For example, the holder 44 may be constructed using polymeric resin materials (e.g., polypropylene, polyethylene, and/or polycarbonate) in a molding process.

The capture medium 42 comprises a material configured to capture and retain a target analyte (e.g., a microorganism or a biological analyte derived from a microorganism). In some embodiments, the capture medium 42 comprises a porous material (e.g., a filter membrane, a porous sheet material) that permits the passage of liquids there through but retains particles of a selected size (e.g., particles that are approximately the size of bacteria such as about 0.5 to about 5 µm, for example). In these embodiments, the capture medium 42 can be one or more of a variety of membrane-type filters (e.g., cellulose acetate filters, nylon filters, nitrocellulose filters, polycarbonate filters, ceramic filters, polysulfone filters, nanofiber filter, and/or a TIPS membrane similar to those described in PCT Patent Publication No. WO2010/078234), for example. Non-limiting examples of suitable membrane-type filters are the VERSAPOR 3000TN membrane (3 µm nominal porosity) and the VERSAPOR 800 membrane (0.8 µm nominal porosity), both available from Pall Life Sciences, Port Washington, N.Y.). In some embodiments, other pore sizes may be useful (e.g., 0.45 µm nominal porosity, 0.2 µm nominal porosity). In some embodiments, the capture medium may comprise two or more layers that may comprise the same material or different materials.

Although membrane-type filters represent a preferred embodiment of the capture medium 42 of the present disclosure, it is also contemplated the capture medium 42 may comprise depth-type filters, which may be relatively thicker than the membrane-type filters illustrated in FIGS. 6-7.

Optionally, in any embodiment, the analyte capture element 40 may comprise a binding partner (e.g., a polyclonal antibody, a monoclonal antibody, a receptor, a lectin, an antibiotic, a bacteriophage, an aptamer) coupled, either directly or indirectly, there to. For example, the analyte capture element 40 may comprise a capture medium 42 (e.g., a membrane) that includes functional groups to which an antibody is covalently or noncovalently attached. In some embodiments, the binding partner may provide the specificity to bind a particular target analyte. In some embodiments, not shown, the analyte capture element 40 may comprise a capture medium 42 comprising a plurality of layers. In some embodiments, the binding partner may be disposed (e.g., on and/or in a particle or a hydrogel) between two layers of the capture medium 42.

In some embodiments (not shown), the analyte-capture element 40 may comprise a particulate material (e.g., a fiber, a particle, a bead) or a nonporous sheet material (e.g., a polymer film) configured to bind to a target analyte. The particulate or sheet materials may be disposed between two layers of the capture medium 42, as described above. In some embodiments, the particulate material may be porous. In some embodiments, the particulate material may be nonporous. In some embodiments, the analyte-capture element 40 may comprise a combination of porous and nonporous particulate materials. In some embodiments, the particulate material may bind the target analyte relatively non-specifically. Certain particulate cell concentration agents are known in the art and are suitable for use in methods of the present disclosure. Nonlimiting examples of suitable cell concentration agents include activated charcoal, hydroxyapatite (Berry et al.; Appl. Environ. Microbiol.; 63:4069-4074; 1997), magnetic beads (Oster et al., J. Magnetism and Magnetic Mat.; 225:145-150; 2001), ferrimagnetic mineral, magnetite, chitosan, and affinity supports. The use of compositions including an immobilized-metal support material to capture or concentrate microorganisms from a sample is described in PCT Patent Publication No. WO 2008/134472, entitled "COMPOSITIONS, METHODS, AND DEVICES FOR ISOLATING BIOLOGICAL MATERIALS", which is incorporated herein by reference in its entirety. In some embodiments, the cell concentration agent may be held on or in a scaffold material such as a wet-laid fiber such as cellulose, for example.

Exemplary particulate materials further include diatomaceous earth and surface treated diatomaceous earth. Specific examples of such concentration agents can be found in commonly assigned PCT Patent Publication No. WO 2009/046191, entitled "MICROORGANISMS CONCENTRATION PROCESS AND AGENT"; the disclosure of which is incorporated herein by reference. When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). In an embodiment, concentration agents can have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged.

In some embodiments, the particulate material may comprise a binding partner coupled thereto and the binding partner may provide the specificity for binding a particular target analyte. In some embodiments, the particulate material may be incorporated into a matrix (e.g., beads entrapped in a fibrous matrix). Non-limiting examples of an analyte capture element comprising a particulate material sandwiched between two layers of porous material are described in PCT Patent Publication No. WO2012/122088, which is incorporated herein by reference in its entirety.

Figure 8:
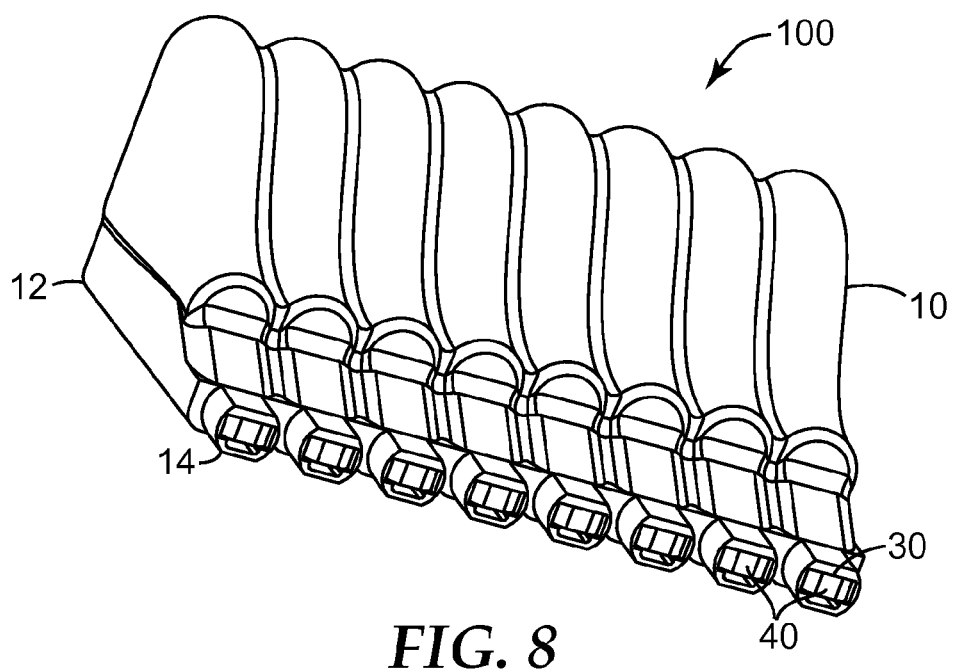
FIG. 8 is a lower perspective view of the apparatus of FIGS. 1-2 with capture elements disposed in an operational position in each of the plurality of channels.

In any embodiment, the analyte capture element can be disposed in an apparatus of the present disclosure. FIG. 8 shows a lower perspective view of the apparatus 100 of FIG. 2, wherein the apparatus 100 has one of a plurality of analyte capture elements 40 disposed in each of the plurality of channels 30 proximate the second end 14 of the body 10.

Figure 9:
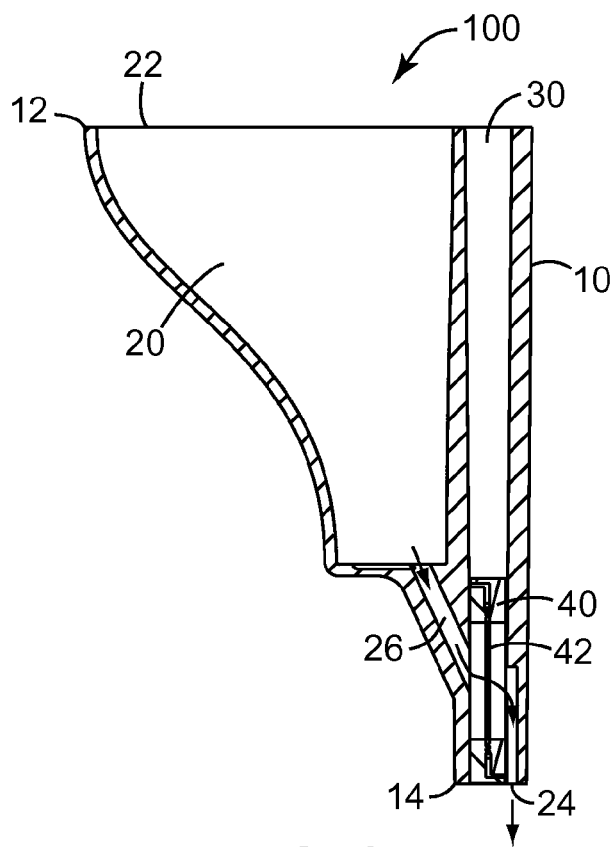
FIG. 9 is a cross-sectional view of the apparatus of FIG. 8, showing a liquid flow path.
Figure 10:
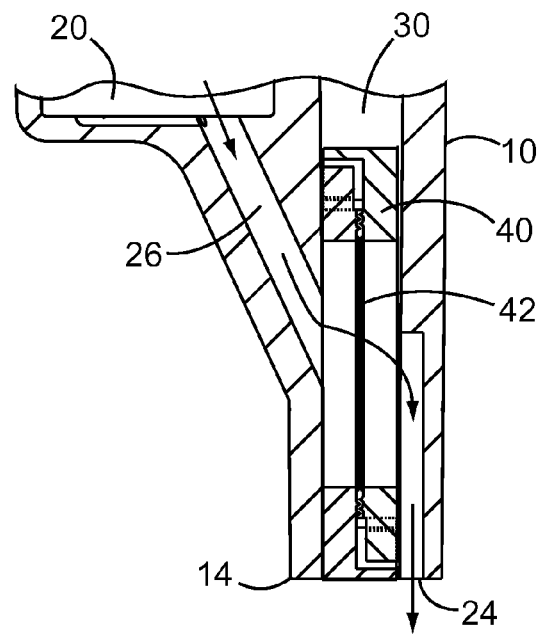
FIG. 10 is a detailed cross-sectional view of the second end of the apparatus of FIG. 9.

FIG. 9 shows a cross-sectional view of the apparatus 100 of FIG. 8. FIG. 10 shows a detailed cross-sectional view of the view of the apparatus 100 of FIG. 9. It can be seen that the analyte capture element 40 is disposed in the channel 30 such that the capture medium 42 transects a flow path (shown by arrows) extending from the sample-receiving opening 22 of the reservoir 20 through the conduit 26 to the effluent discharge opening 24. Thus, in the illustrated embodiment, if the capture medium 42 is a porous membrane, for example, a liquid sample (not shown) passing from the first end 12 to the second end 14 of the body 10 passes through the capture medium 42. If the liquid sample comprises a target analyte (e.g., a target microorganism or a portion thereof), the target analyte can be captured by the analyte capture element 40.

Figures 11A, 11B:
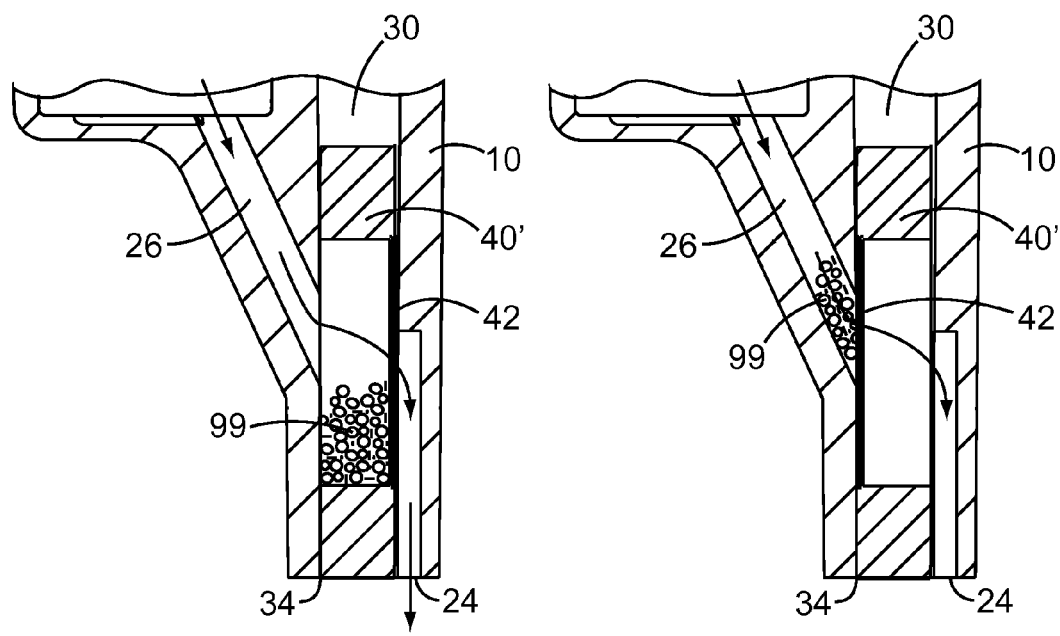
FIG. 11A is a detailed cross-sectional view of the second end of the apparatus of FIG. 8 comprising an embodiment of an alternative analyte capture element disposed in the chamber in a first orientation.
FIG. 11B is a detailed cross-sectional view of the second end of the apparatus of FIG. 8 comprising the alternative analyte capture element disposed in the chamber in a second orientation.

FIGS. 11A and 11B each show detailed cross-sectional side views of the second end 14 of an apparatus 100 of the present disclosure. In these embodiments, an alternative analyte capture element 40' is disposed in the channel 30 proximate the second end 14 of the body 10. In contrast to the analyte capture element 40 of FIGS. 6 and 7, which comprises a capture medium 42 positioned approximately along a longitudinal midline of the analyte capture element 40, the analyte capture element 40' comprises a capture medium 42 (e.g., a porous membrane, positioned along one edge of the analyte capture element 40'.

Thus, the capture medium 42 can be positioned in the flow path proximate the effluent discharge opening 24 (as shown in FIG. 11A) or the capture medium 42 can be positioned in the flow path proximate the conduit 26 (as shown in FIG. 11B). Using the configuration shown in FIG. 11B, particulate material 99 is trapped in the conduit 26 by the capture medium 42 and the resulting trapped particulate material 99 can be substantially retained in the conduit 26 as the analyte capture element 40' is ejected from the second channel opening 34 of the body 10.

In contrast, using the configuration shown in FIG. 11A, particulate material 99 is trapped in the channel 30 by the capture medium 42 and the resulting trapped material can be substantially ejected with the analyte capture element 40' when the capture element 40' is ejected from the second channel opening 34 of the body 10. This particulate material 99 may be ejected with the analyte capture element 40 and, optionally, can be processed likewise to determine whether a target analyte is present in the particulate material 99 trapped by the analyte capture element 40. A skilled person will recognize this feature provides increased sensitivity for the detection of target analyte in the sample material.

Figure 12A:
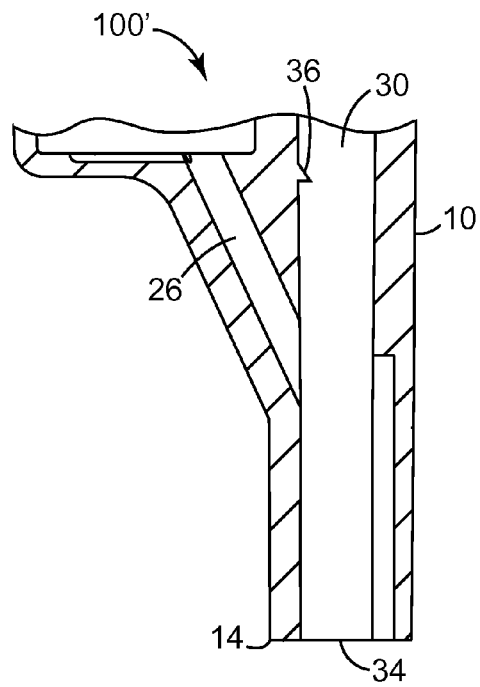
FIG. 12A is a detailed cross-sectional view of the second end of the apparatus comprising a channel with a first retention structure.

In any embodiment, an apparatus according to the present disclosure may further comprise a structure to retain (e.g., releasably retain) the analyte capture element at a predetermined location in a channel. FIG. 12A shows a cross-sectional side view of the second end 14 of one embodiment of an apparatus 100' comprising a first retention structure 36 disposed in the channel 30 such that the conduit 26 opens into the channel 30 at a location between the first retention structure 36 and the second channel opening 34. The first retention structure 36 may be formed from the same material as the body 10 of the apparatus 100', optionally during a molding process that forms the body 10. Alternatively, the first retention structure 36 may be attached (e.g., via an adhesive, ultrasonic welding, or other means known in the art) after the body 10 is formed. When an analyte capture element (analyte capture element 40, shown in FIG. 12C) is inserted into the channel 30 (e.g., via the second channel opening 34), it meets resistance to further movement into the channel 30 when it contacts the first retention structure 36. This resistance signals that the analyte capture element is properly positioned for use in the apparatus 100' (e.g., the analyte capture element is positioned at a location that is in fluid communication with a flow path that intersects the channel 30 in which the analyte capture element is disposed).

Optionally, the first retention structure 36 and/or the analyte capture element can configured so that the analyte capture element can continue moving through the channel 30 past the first retention structure 36. For example, the first retention structure 36 and/or the analyte capture element can be fabricated from a relatively soft material (e.g., polypropylene, polyethylene) such that the first retention structure 36 and/or the analyte capture element can deform sufficiently to permit the analyte capture element to move while contacting the first retention structure 36, provided the analyte capture element is urged with sufficient force to overcome the frictional resistance.

Figure 12B:
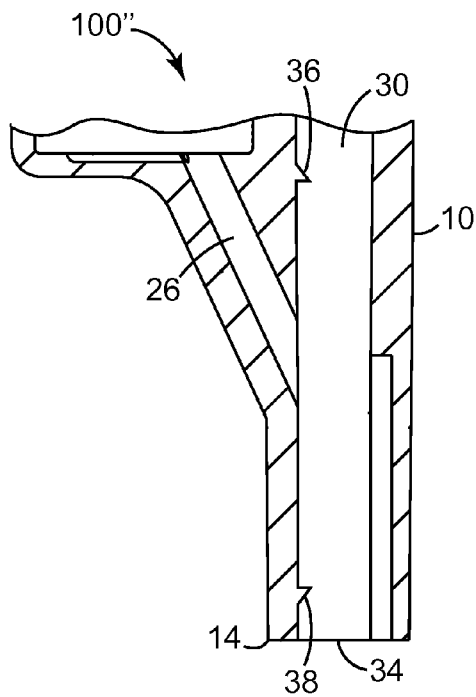
FIG. 12B is a detailed cross-sectional view of the second end of the apparatus of FIG. 12A wherein the channel further comprises a second retention structure.
Figure 12C:
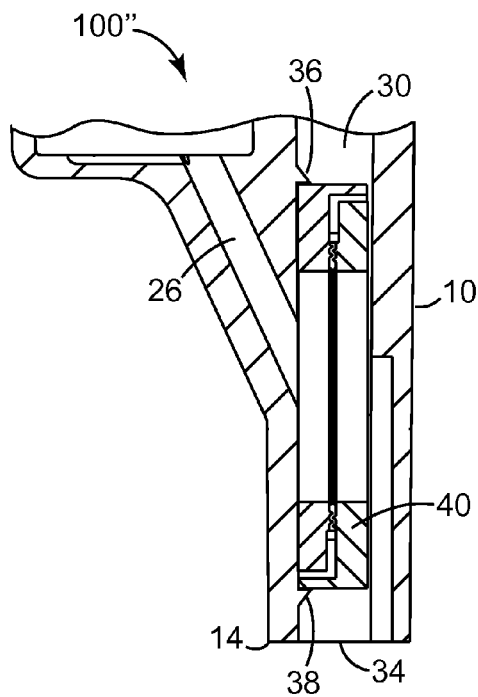
FIG. 12C is a detailed cross-sectional view of the second end of the apparatus of FIG. 12B with an analyte capture element operably disposed in the channel.

Alternatively, or in addition to having a first retention structure, any apparatus according to the present disclosure may further comprises a second retention structure to retain (e.g., releasably retain) the analyte capture element at a predetermined location in a channel. FIG. 12B shows a cross-sectional side view of the second end 14 of one embodiment of an apparatus 100" comprising a first retention structure 36 and a second retention structure 38 disposed in the channel 30. The second retention structure 38 is positioned between the conduit 26 and the second channel opening 34. The second retention structure 38 may be formed from the same material as the body 10 of the apparatus 100", optionally during a molding process that forms the body 10. Alternatively, the second retention structure 38 may be attached (e.g., via an adhesive, ultrasonic welding, or other means known in the art) after the body 10 is formed. When an analyte capture element (analyte capture element 40, shown in FIG. 12C) is inserted into the channel 30 (e.g., via the second channel opening 34), it meets resistance to further movement into the channel 30 when it contacts the second retention structure 38. Using sufficient force, the analyte capture element and/or the second retention element 38 can deform sufficiently to permit the analyte capture element to continue moving into the channel 30 until it contacts the first retention element 36. The analyte capture element 40 is properly positioned for use in the apparatus 100" (e.g., the analyte capture element is releasably engaged at a location that is in fluid communication with a flow path that intersects the channel 30 in which the analyte capture element 40 is disposed, as shown in FIG. 12C).

Figure 18:
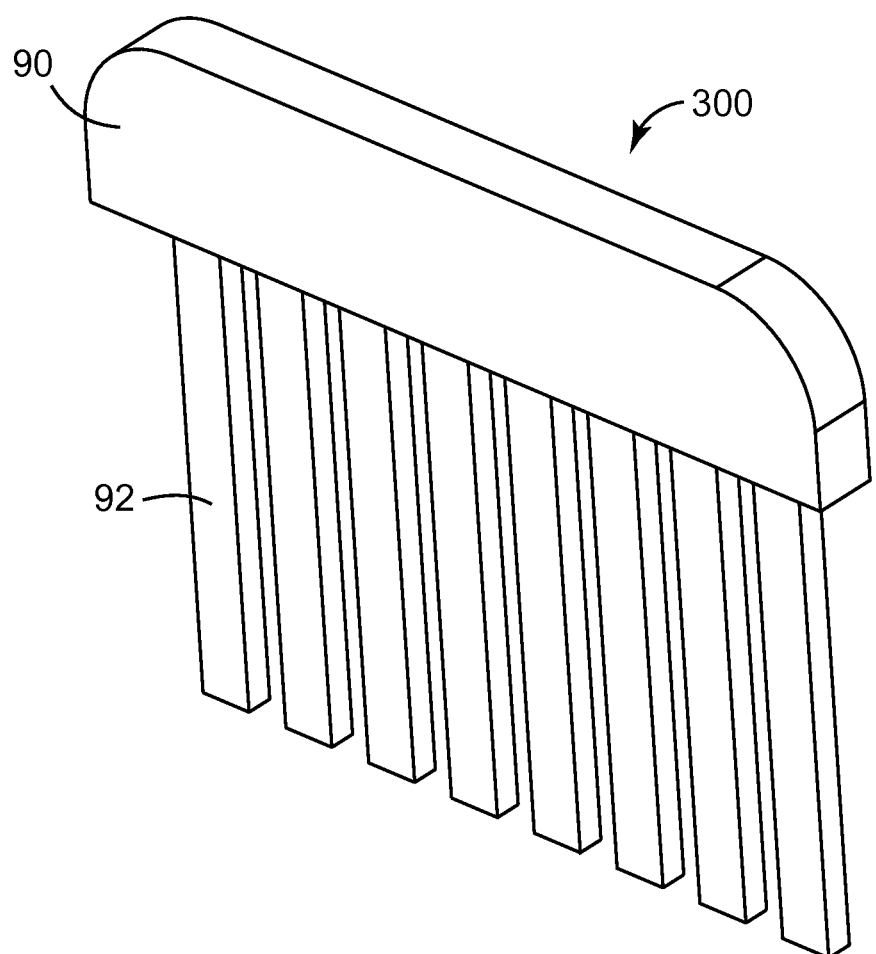
FIG. 18 is a perspective view of one embodiment of a discharge element according to the present disclosure.

When used in a method according to the present disclosure, an analyte capture element can be ejected from the channel to detect the presence or absence of a target analyte retained by the analyte capture element. The ejection process can be facilitated by using a discharge element that is configured to move through the channel, contact the analyte capture element, and urge the analyte capture element out of the channel. FIG. 18 shows one embodiment of a capture element discharger 300 comprising an optional handle 90 and one or more posts 92. The posts 92 are suitably dimensioned and spaced apart such that they can be inserted (e.g., inserted simultaneously) into a plurality of first channel openings in the apparatus of FIG. 1. After inserting the posts 92, the handle 90 can be used to urge the post 92 toward the body of the apparatus, causing the post 92 to move through the channel until it contacts an analyte capture element, if present, in the channel. Urging the post 92 further into the channel causes the post 92 to eject the analyte capture element out the second channel opening 34 of the body 10.

The discharge element 300 may be fabricated as a unitary device having one or more posts or the handle may be fabricated separately and coupled to one or more posts 92 using any suitable coupling means (e.g., adhesive, sonic weld, clip, staple, pin, screw, or the like) known in the art. Alternatively, the posts 92 can be fabricated individually, optionally with a handle 90, or individual posts 92 may be coupled to a handle 90 as described above. The parts (handle 90 and posts 92) may be fabricated from wood, metal, or plastic, for example. The posts 92 can preferably be dimensioned to extend approximately at least the length of the channel, thereby ensuring it can fully displace and eject the analyte capture element from the channel. In a preferred embodiment, the posts 92 are shaped and dimensioned to seal the conduit while ejecting the analyte capture element from the apparatus.

Figure 13:
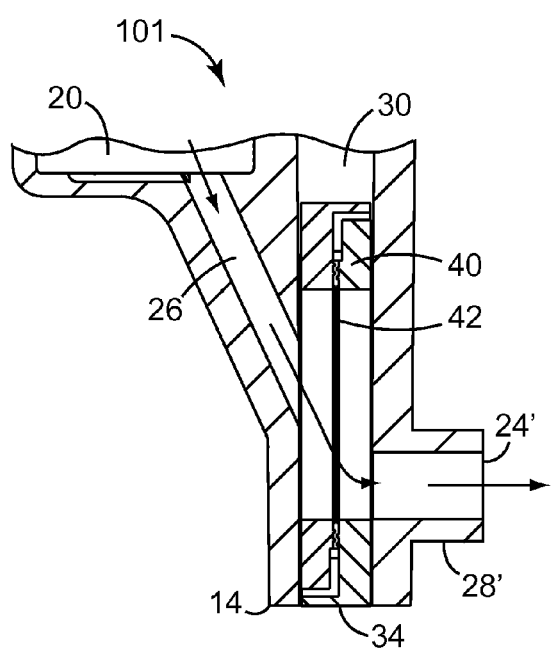
FIG. 13 is a detailed cross-sectional view of the second end of one embodiment of an apparatus comprising at the second end separate openings for the channel and the effluent discharge.

In some embodiments, the second channel opening and effluent discharge opening comprise separate openings proximate the second end of the body. FIG. 13 shows a cross-sectional view of the second end 14 of one embodiment of an apparatus 101 comprising separate openings for the second channel opening 34 and the effluent discharge opening 24'. Also shown in FIG. 13 are a flow path (arrows), a portion of the reservoir 20, the conduit 26 that fluidically connects the reservoir 20 with the channel 30, a portion of the channel 30, the outlet 28', and an analyte capture element 40 comprising a capture medium 42 (e.g., a porous membrane). In the illustrated embodiment, the outlet 28' extends from the body 10 sufficiently enough to permit attachment to a vacuum source (e.g., tubing connected to a vacuum pump, not shown). Similar to other embodiments of the disclosure, the analyte capture element 40 is slideably engaged in the channel 30 and can be ejected from the channel 30 for analysis after a liquid sample (not shown) has contacted the analyte capture element 40. In these embodiments, optionally, the apparatus may further comprise a frangible seal (not shown) proximate the second channel opening. For example, the frangible seal can be fabricated from a polymeric or metal film and can be coupled to the second end of the body via a pressure sensitive adhesive, for example.

Figure 14:
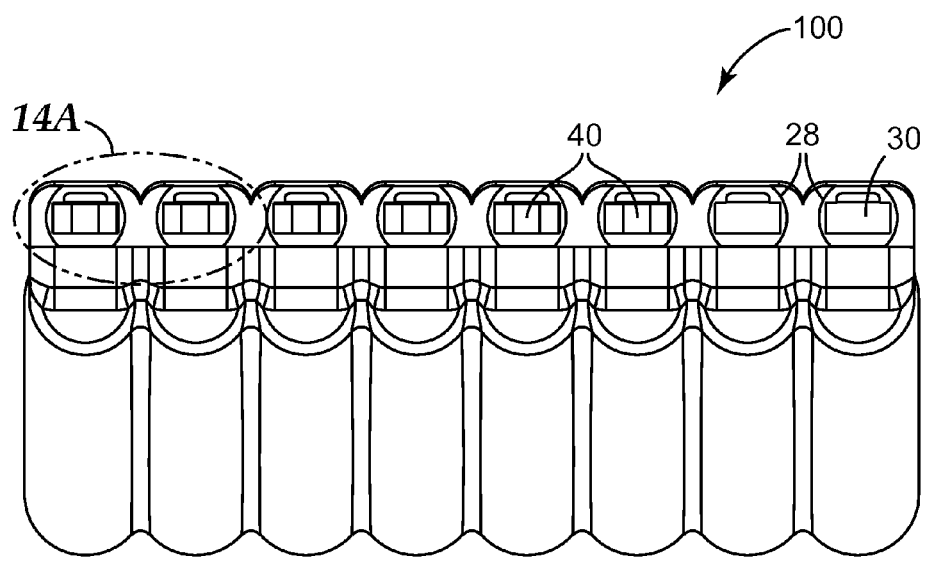
FIG. 14 is a bottom view of the apparatus of FIG. 2 with analyte capture elements disposed in all but two of the channels.
Figure 14A:
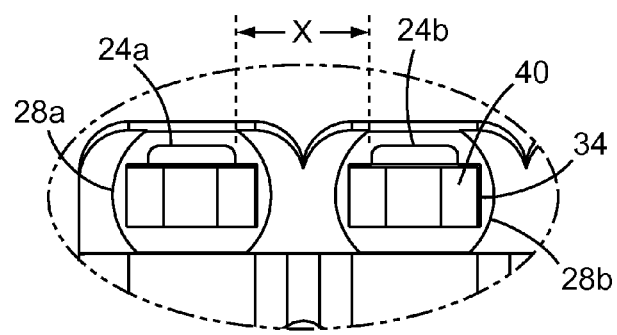
FIG. 14A is a bottom detailed view of a portion of the body of FIG. 14 showing a minimum distance between the effluent discharge openings of adjacent outlets.

The plurality of outlets in the apparatus of the present disclosure are spaced apart to reduce the probability of cross-contamination between adjacent flow paths of the apparatus and/or liquid samples passing through adjacent flow paths in the apparatus. FIG. 14 shows a bottom view of the apparatus 100 of FIG. 8. FIG. 14A shows a detailed view of two adjacent outlets 28. Each of the adjacent outlets 28 has an analyte capture element 40 disposed in the channel 30 proximate the second channel opening 34. Each of the adjacent outlets (outlets 28a and 28b, respectively) also comprises an effluent discharge opening (24a and 24b, respectively). There exists a minimum distance ("X") between two adjacent effluent discharge openings (e.g., openings 24a and 24b, respectively).

Figure 15:
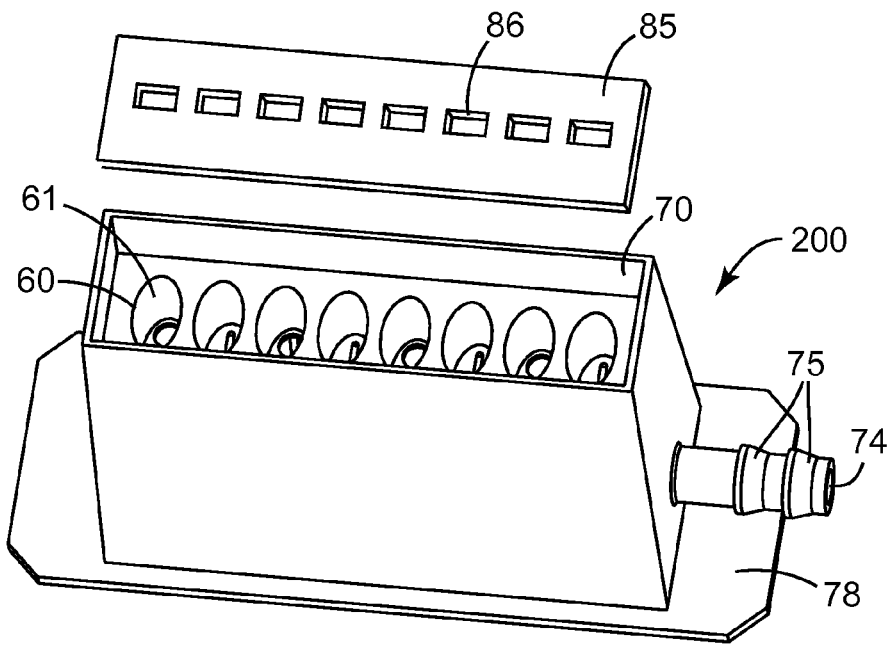
FIG. 15 is an exploded upper perspective view of one embodiment of a waste receptacle according to the present disclosure.
Figure 16:
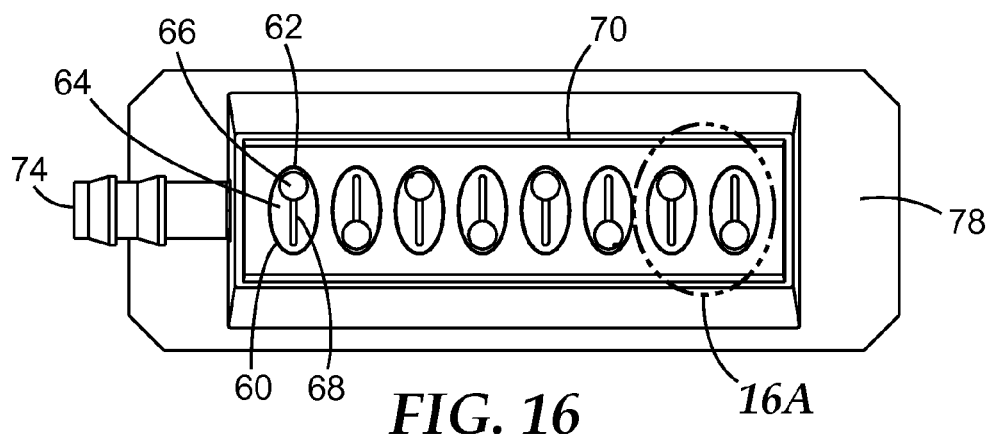
FIG. 16 is a top view of the waste receptacle of FIG. 15.

Any apparatus of the present disclosure, with an analyte capture element disposed in at least one of the plurality of channels, can be used in an assembly for processing a sample. The assembly can comprise a waste receptacle configured to be operationally coupled to the apparatus. When operationally coupled to the apparatus, the waste receptacle can receive a liquid effluent from at least one of the plurality of outlets of the apparatus. FIG. 15 shows an upper perspective view and FIG. 16 shows a top view of one embodiment of a waste receptacle 200 according to the present disclosure. The waste receptacle 200 comprises a plurality of spaced-apart chambers 60. Preferably, the number of chambers 60 corresponds to the number of outlets present in the apparatus to which the waste receptacle 200 will be operationally coupled. The spacing and dimensions of the chambers 60 are selected such that the chambers 60 can receive liquid streams from at least two adjacent outlets and substantially prevent the separate liquid streams from contacting each other.

The waste receptacle 200 optionally may comprise a flange 70. The flange 70 may be configured to form a tight fit with the apparatus (not shown) to facilitate a sufficient seal to prevent leakage and to permit vacuum suction to be transmitted from the waste receptacle 200 to the apparatus. In addition, the flange 70 may position and retain an optional gasket 85. The gasket 85 comprises holes 86 dimensioned to receive the outlets of any one of the apparatuses described herein. The gasket 85 can be fabricated from a conformable material (e.g., butyl rubber) and can facilitate the formation of a vacuum seal between the waste receptacle 200 and an apparatus (not shown) according to the present disclosure. Optionally, the waste receptacle 200 further may comprise a vent 74. The vent 74 may be adapted to be connected to a source of negative pressure (e.g., a vacuum pump). The adaptations may comprise for example, shaping and dimensioning the vent 74 so that it can be attached to a vacuum hose. In addition, the vent 74 may comprise ribs 75 to retain a vacuum hose. Optionally, the waste receptacle 200 may further comprise a receptacle base 78 to support the receptacle on a surface.

Each of the plurality of chambers 60 has at least one wall 61 defining an outlet-receiving opening 62. Optionally, the chamber further may comprise a floor 64. In some embodiments, the floor 64 may be substantially planar. The at least one wall 61 and, if present, optional floor 64 define an interior volume of the chamber 60. Each chamber 60 further comprises a drain 66, which is an opening to direct the flow of liquid (e.g., by gravity or by vacuum suction) out of the chamber 60. In the illustrated embodiment, the drains 66 are positioned in the floor 64 of the chamber 60. Optionally, the floor 64 further may comprise a trough 68 to direct the flow of liquid along the floor 64 to the drain 66. In an alternative configuration (not shown), the drain openings may be located in the walls of the chambers.

Figure 16A:
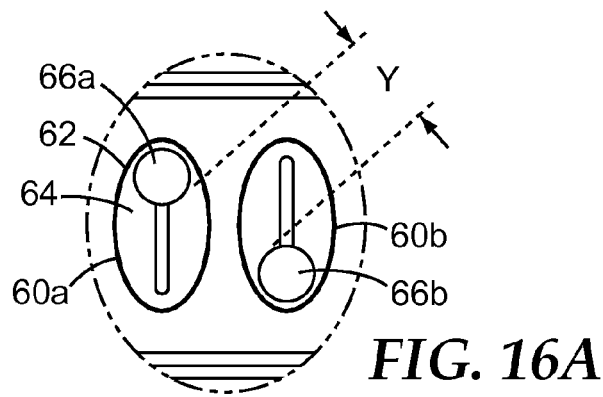
FIG. 16A is a detailed view of a portion of the waste receptacle of FIG. 15 showing a minimum distance between the drains of adjacent chambers.

FIG. 16A shows a detailed top view of two adjacent chambers (60a and 60b, respectively) in the waste receptacle 200 of FIGS. 15 and 16. The chambers 60a and 60b each have a wall 61, floor 64, drain (66a and 66b, respectively), and trough 68. Similar to the adjacent effluent discharge openings of the apparatus (shown in detail in FIG. 14A), there exists a minimum distance ("Y") between two adjacent drains (e.g., 66a and 66b, respectively).

The waste receptacle 200 can be fabricated by injection molding, for example, from polymeric material (e.g., polyethylene, polypropylene, polystyrene, and/or polycarbonate). Alternatively, the waste receptacle 200 can be fabricated using glass or metal.

Figure 17:
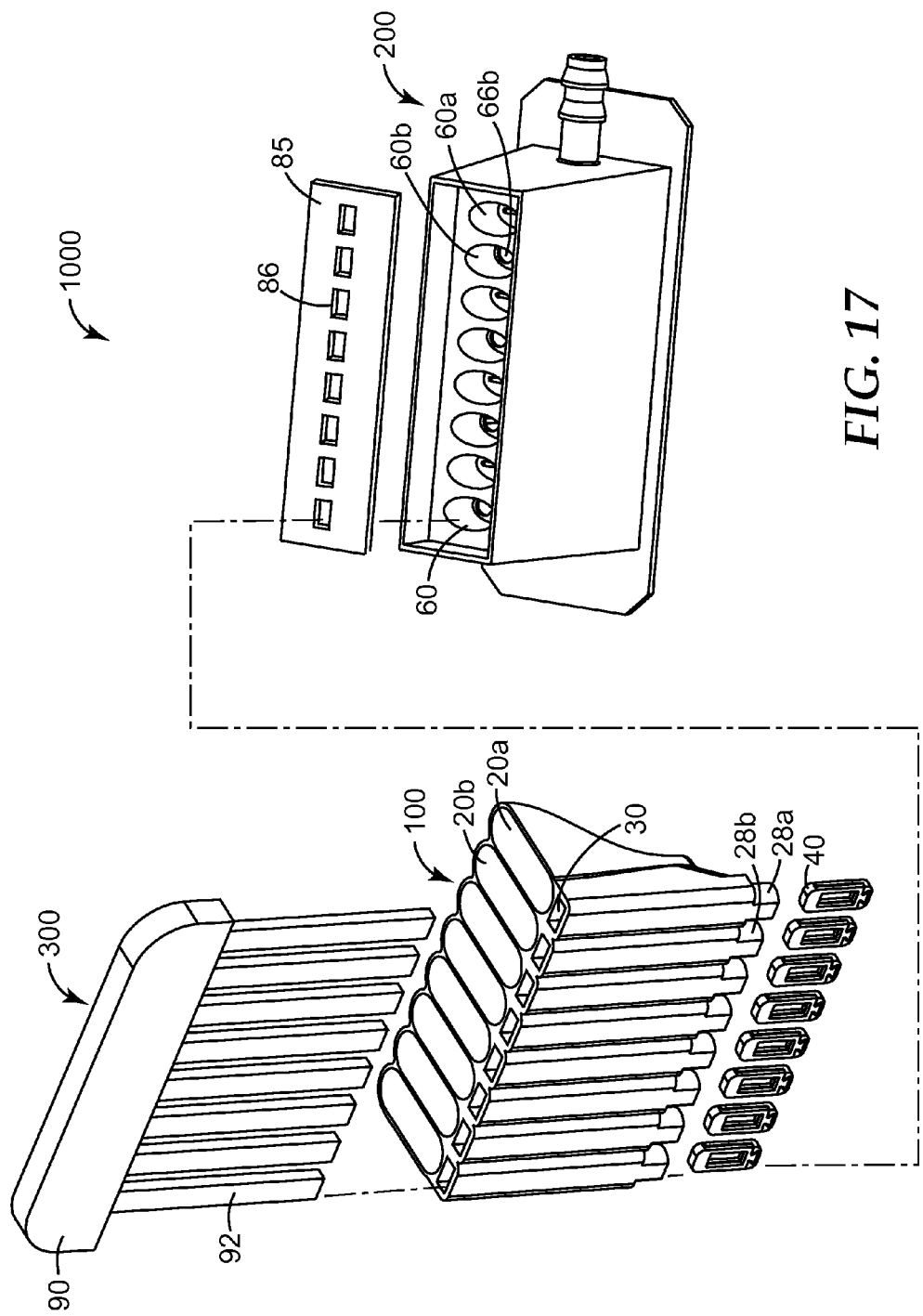
FIG. 17 is an exploded perspective view of one embodiment of an assembly for processing a sample according to the present disclosure.

FIG. 17 shows an exploded perspective view of one embodiment of an assembly 1000 for processing a sample, according to the present disclosure. The assembly 1000 comprises an apparatus 100 comprising a plurality of reservoirs 20 according to any one of the embodiments described herein, at least one capture element 40 slideably engaged in one of the channels 30, and a waste receptacle 200 comprising a plurality of chambers 60 according to any one of the embodiments described herein. The apparatus 100 comprises a first reservoir 20a in fluidic communication with a first outlet 28a and a second reservoir 20b in fluidic communication with a second outlet 28b. The waste receptacle 200 comprises a first chamber 60a and a second chamber 60b, the first chamber 60a having a first interior volume and the second chamber 60b having a second interior volume. The first chamber 60a comprises a first drain (not shown) and second the chamber 60b comprises a second drain (66b).

Optionally, when the apparatus 100 and the waste receptacle 200 are operationally coupled, at least a portion of the first outlet 28a is disposed in the first interior volume of the first chamber 60a and at least a portion of the second outlet 28b is disposed in the second interior volume of the second chamber 60b. Advantageously, this configuration substantially can prevent cross-contamination of separate liquid streams passing through (e.g., passing through either simultaneously or sequentially) the first outlet 28a and second outlet 28b, respectively, or cross-contamination of analyte capture elements disposed in adjacent outlets, by physically isolating the respective outlets (and analyte capture elements disposed therein) in separate chambers.

The first and second outlets (28a and 28b, respectively) each comprise a first effluent discharge opening (not shown) and a second effluent discharge opening (not shown), respectively, as described herein. There exists in the assembly 1000 a first shortest distance between the first effluent discharge opening and the second effluent discharge opening (for example, as shown in FIG. 14A). In addition, there exists in the assembly 1000 a second shortest distance between the first drain and the second drain (for example, as shown in FIG. 16A. Thus, in a preferred embodiment of the assembly 1000, the first shortest distance is shorter than the second shortest distance. Advantageously, this configuration further reduces the probability of cross-contamination between separate liquid streams passing through (e.g., passing through either simultaneously or sequentially) the first outlet 28a and second outlet 28b, respectively, by causing greater physical separation of the liquid streams as they pass out of the respective drains.

Optionally, in any embodiment of the assembly 1000, each of the plurality of chambers 60 may comprise a substantially planar floor, as described herein. In any embodiment of the assembly 1000, the floor may comprise the drain. In any embodiment of the assembly 1000, the floor further may comprise a trough (not shown), as described herein. In any embodiment of the assembly 1000, the waste receptacle 200 may be adapted to be coupled to a source of negative pressure, as described herein.

The present disclosure includes a method of detecting a presence or an absence of an analyte in a sample. The method comprises providing a liquid sample and an apparatus or an assembly, said apparatus or assembly with at least one analyte capture element moveably (e.g., slideably) engaged in a channel according to any of the embodiments described herein.

The method of the present disclosure further comprises contacting the liquid sample with the at least one analyte capture element. Typically, contacting the liquid sample with the at least one analyte capture element comprises loading the sample into a reservoir that is in fluidic communication with the at least one analyte capture element and permitting the liquid sample to flow through the apparatus from the reservoir to the effluent discharge opening and out of the apparatus. While flowing from the reservoir to the effluent discharge opening, the liquid sample contacts the analyte capture element. In certain preferred embodiments, the liquid sample passes through the analyte capture element while contacting it. In some embodiments, the liquid sample can pass through the device by gravity flow. In some embodiments, the liquid can be urged to pass through the apparatus by applying positive or negative pressure. Accordingly, in some embodiments, the method further can comprise the step of operably connecting the apparatus or the assembly to a source of negative pressure, as described herein.

In some embodiments, the at least one capture element comprises a porous medium. In these embodiments, contacting the liquid sample with the at least one capture element can comprise passing the liquid sample through the porous medium.

The method of the present disclosure further comprises ejecting the at least one analyte capture element from the channel. Ejecting the at least one analyte capture element can comprise sliding the capture element out of an opening at the second end of the apparatus (e.g., the second channel opening shown in FIG. 3). In some embodiments, an accessory tool (e.g., forceps, a pipette tip) may be used to grasp or pry the analyte capture element out of the channel. In some embodiments, ejecting the at least one analyte capture element from the channel can comprises moving a portion of a discharge element through a portion of the channel to eject the analyte capture element from the channel. The discharge element can comprise a portion (e.g. a post, such as a solid post, shaped and dimensioned to fit in the channel) configured to move through the channel, contact the analyte capture element, and urge the analyte capture element out of the channel, as described herein.

The method of the present disclosure further comprises detecting a presence or an absence an analyte retained from the sample by the analyte capture element. Detecting the presence or absence of an analyte can comprise detecting the presence or absence of an analyte associated (e.g., exclusively associated) with a cell of interest (e.g., a microbial cell). The analyte may comprise a nucleotide (e.g., ATP), a nucleic acid (e.g., DNA, RNA, mRNA, and/or an oligonucleotide), an enzyme, or an antigen associated with a cell of interest. Thus, detecting a presence or an absence an analyte retained from the sample may comprise detecting a nucleotide, a nucleic acid, an enzyme, and/or an antigen associated with a cell of interest. A person having ordinary skill in the art will recognize suitable detection methods that can be used to detect an analyte captured by the analyte capture element.

Optionally, in any embodiment, the method further can comprise processing the at least one analyte capture element and/or sample material associated therewith to permeabilize a cell. Before and/or after the analyte capture element is ejected from the channel, the analyte capture element and, if present, any sample material associated therewith can be treated to permeabilize a cell. This can be performed, for example, by contacting the analyte capture element and/or sample material with a lysing agent (e.g., a detergent, an enzyme). After the capture element is ejected from the channel, the analyte capture element and, if present, any sample material associated therewith can be treated mechanically (e.g., by heat, sonication, freeze/thaw) to permeabilize a cell. Permeablizing the cells can improve the detection of an analyte associated with a cell of interest.

In any embodiment, the method further can comprise the step of coupling at least one outlet to a container. The container may be a reaction tube or a linear array of reaction tubes, for example, in which the analyte capture element can be processed to detect the presence or absence of an analyte. In these embodiments, ejecting the at least one analyte capture element from the channel can comprise ejecting the analyte capture element into the container. Advantageously, if the outlets are spaced apart, shaped, and dimensioned to fit into a predetermined container (e.g., a reaction tube) or linear array of containers, this feature of the apparatus and method can substantially prevent contamination of the analyte capture element with materials that were not present in the sample when the analyte capture element is transferred to a container.

It will be recognized by a person having ordinary skill in the art that the apparatuses or assemblies of the present disclosure can be used according to the method to process a plurality of samples. Optionally, the plurality of samples may be processed simultaneously.

In some embodiments, the analyte may be a whole microorganism such as a bacterium, for example. In some embodiments, the analyte may be a living microorganism. In these embodiments, it may be desirable to detect the microorganism by culture techniques. Accordingly, the microorganisms may be detached or eluted from the analyte-capture element by rinsing and/or homogenizing the analyte-capture element in a suspending medium (water, buffer, buffered saline, liquid culture media). The liquid suspending medium could be used to inoculate culture media (e.g., the appropriate agar culture medium) to determine the presence, absence or quantity of target microorganisms that were in the original sample. In some embodiments, the analyte-capture medium could be transferred directly onto culture media for growth and analysis. Accordingly, when the analyte-capture element is separated from the apparatus by ejecting the analyte-capture element into a container, the container may include a suspending medium therein.

In some embodiments, the analyte may be a whole microorganism or a portion of a microorganism (e.g., a cell wall or a fragment thereof, a cell membrane or a fragment thereof, a protein, or a polysaccharide). In these embodiments, it may be desirable to detect the analyte using an immunodiagnostic method (e.g., ELISA, immunochromatography). Accordingly, when the analyte-capture element is separated from the apparatus by ejecting the analyte-capture element into a container, the container may include a suspending medium, a cell lysis reagent (e.g., an acid, a base, a detergent, an enzyme, a protease, lysozyme, lysostaphin), and/or an analyte-specific binding partner (e.g., an antibody, a receptor) therein.

In some embodiments, the analyte may be an enzyme or an enzyme substrate (e.g., ATP) associated with a particular microorganism or group of microorganisms. In these embodiments, it may be desirable to detect the analyte using an enzyme assay. Accordingly, when the analyte-capture element is separated from the apparatus by ejecting the analyte-capture element into a container, the container may include a suspending medium, a cell lysis reagent (e.g., an acid, a base, a detergent, an enzyme, a protease, lysozyme, lysostaphin), an enzyme (e.g., luciferase, adenylate kinase) and/or an enzyme substrate (e.g., a luciferin, a chromogenic enzyme substrate, or a fluorogenic enzyme substrate) therein.

In some embodiments, the analyte may be a microorganism-associated polynucleotide (e.g., DNA or RNA). In these embodiments, it may be desirable to detect the analyte using nucleic acid detection methods known in the art (e.g., PCR, rtPCR, LCR, NASBA, blot analysis). Accordingly, when the analyte-capture element is separated from the apparatus by ejecting the analyte-capture element into a container, the container may include a suspending medium, a cell lysis reagent (e.g., an acid, a base, a detergent, an enzyme, a protease, lysozyme, lysostaphin), an analyte-specific probe, an analyte-specific primer and/or an enzyme and a reagent for amplifying or labeling a polynucleotide therein.

In some embodiments, the method further can comprise an enrichment step. The enrichment step can comprise providing a culture medium to facilitate the growth of a target microorganism and a latent effervescent body comprising a selective agent, as described in PCT Patent Publication No. WO2012/092123, which is incorporated herein by reference in its entirety.

The present disclosure also provides a kit for processing a sample. The kit can comprise any apparatus according to the present disclosure to be used in a method of processing a sample according to the present disclosure. In some embodiments, the kit further may comprise one or more analyte capture elements configured to be slideably engaged in a channel of the apparatus. In some embodiments, the kit further may comprise an analyte capture element discharger. In any embodiment, the kit further may comprise a reagent. The reagent may comprise a cell lysis agent, or a detection agent. The detection agent may comprise, for example, an oligonucleotide, a labeled oligonucleotide, an enzyme substrate, a binding partner (e.g., an antibody, a receptor), and/or a labeled binding partner.

EMBODIMENTS

Embodiment A is an apparatus for processing a sample, comprising:
a body having a first end and a second end opposite the first end, the body comprising:
a plurality of spaced-apart reservoirs in a linear array, each reservoir comprising a sample-receiving opening;
a plurality of spaced-apart effluent discharge openings, each effluent discharge opening in fluid communication with one of the plurality of sample-receiving openings via a flow path;
a plurality of channels, each channel intersecting one of the flow paths;
wherein each channel comprises a second channel opening proximate the second end;
wherein each channel is dimensioned to receive a analyte capture element; and
a plurality of spaced-apart outlets extending from the body, each of the outlets comprising one of the second channel openings.

Embodiment B is the apparatus of Embodiment A, wherein each of the outlets further comprises one of the effluent discharge openings.

Embodiment C is the apparatus of Embodiment A or Embodiment B, wherein the effluent discharge opening and the second channel opening define a common opening.

Embodiment D is the apparatus of any one of the preceding Embodiments, further comprising an analyte capture element slideably engaged in a channel at a location that is in fluid communication with the flow path that intersects the channel in which the analyte capture element is disposed.

Embodiment E is the apparatus of Embodiment D, wherein the analyte capture element comprises a holder with a capture medium attached thereto.

Embodiment F is the apparatus of any one of the preceding Embodiments, wherein the apparatus further comprises a first retention structure disposed in a channel, wherein the first retention structure is configured to position a analyte capture element, if present, at a location in the channel where the analyte capture element is in fluid communication with the flow path that intersects the channel.

Embodiment G is the apparatus of Embodiment F, further comprising a second retention structure disposed in the channel, wherein the first and second retention structures are configured to releasably hold the analyte capture element, if present, at a location where the analyte capture element is in fluid communication with the flow path.

Embodiment H is the apparatus of any one of Embodiments D through G, wherein the analyte capture element comprises an analyte binding reagent.

Embodiment I is the apparatus of any one of Embodiment D through H, wherein the apparatus is configured such that substantially all liquid passing through the flow path from the sample-receiving opening to the effluent discharge opening passes through the analyte capture element.

Embodiment J is the apparatus of any one of Embodiments E through I;
wherein the holder comprises a first face, a second face opposite the first face, and a longitudinal plane between the first face and the second face;
wherein the capture medium is disposed in the holder substantially along the longitudinal plane.

Embodiment K is the apparatus of any one of Embodiments F through I;
wherein the holder comprises a first face, a second face opposite the first face;
wherein the capture medium is disposed on the holder substantially along the first or second face.

Embodiment L is the apparatus of any one of Embodiments E through I;
wherein the holder comprises a first face, a second face opposite the first face, and a longitudinal plane between the first face and the second face;
wherein the capture medium is disposed in the holder in a plane that is oriented from a portion of the first face to a portion of the second face.

Embodiment M is the apparatus of any one of the preceding Embodiments, wherein the channel extends from the second channel opening to a first channel opening.

Embodiment N is the apparatus of Embodiment M, wherein the first channel opening is disposed at the first end.

Embodiment O is the apparatus of any one of the preceding Embodiments, further comprising an analyte capture element discharger comprising a post, wherein a portion of the post is disposed in the channel, wherein the discharger is configured to move through the channel and to urge an analyte capture element, if present in the channel, out of the second channel opening.

Embodiment P is the apparatus of any one of the preceding Embodiments, wherein the sample-receiving opening of each of the plurality of chambers is covered with a pierceable seal.

Embodiment Q is the apparatus of any one of the preceding Embodiments, further comprising a prefilter disposed in a flow path between the sample-receiving opening of the flow path and the channel that intersects the flow path.

Embodiment R is the apparatus of any one of the preceding Embodiments, wherein each outlet of the plurality of outlets is shaped, dimensioned, and spaced apart such that the plurality of outlets can be received into a linear array of two or more tubes.

Embodiment S is the apparatus of Embodiment R, wherein the tubes in the linear array have a center-to-center distance of about 9 mm or less.

Embodiment T is the apparatus of embodiment S, wherein each of the tubes has a circular opening, wherein the circular opening has an inner diameter of about 2 mm to about 7 mm.

Embodiment U is an assembly, comprising:
the apparatus of any one of the preceding Embodiments, wherein the apparatus comprises:
a first reservoir having a first sample-receiving opening and a first outlet having a first effluent discharge opening;
a second reservoir adjacent the first reservoir, the second reservoir having a second sample-receiving opening and a second outlet having a second effluent discharge opening;
a waste receptacle operably coupled thereto;
wherein the waste receptacle comprises a plurality of spaced-apart chambers, wherein the plurality of spaced-apart chambers comprises:
a first chamber having a first interior volume and a first drain;
a second chamber adjacent the first chamber, the second chamber having a second interior volume and a second drain; and
an analyte capture element slideably engaged in one of the channels;
wherein, when the apparatus and the waste receptacle are operably coupled, a first liquid flow path extends from the first sample-receiving opening to the first drain, and a second liquid flow path extends from the second sample-receiving opening to the second drain;
wherein a first shortest distance between the first effluent discharge opening and the second effluent discharge opening is shorter than a second shortest distance between the first drain and the second drain.

Embodiment V is the assembly of Embodiment U wherein, when the apparatus and the waste receptacle are operably coupled, at least a portion of the first outlet is disposed in the first interior volume and at least a portion of the second outlet is disposed in the second interior volume.

Embodiment W is the assembly of Embodiment U or Embodiment V, wherein each of the plurality of chambers comprises a substantially planar floor, wherein the floor comprises the drain.

Embodiment X is the assembly of embodiment W, wherein the floor further comprises a trough extending along a portion of the floor to the drain.

Embodiment Y is the assembly of any one of Embodiments U through X, wherein the waste receptacle is adapted to be coupled to a source of negative pressure.

Embodiment Z is a method of detecting a presence or an absence of an analyte in a sample, the method comprising:
providing a liquid sample and an apparatus of any one of embodiments 4 through 20 or the assembly of Embodiments U through Y, wherein at least one analyte capture element is movably engaged a channel;
contacting the liquid sample with the at least one analyte capture element;
ejecting the at least one analyte capture element from the channel; and
detecting a presence or an absence an analyte retained from the sample by the analyte capture element.

Embodiment AA is the method of Embodiment Z, wherein contacting the liquid sample with the at least one analyte capture element comprises loading the sample into a reservoir that is in fluidic communication with the at least one analyte capture element.

Embodiment BB is the method of Embodiment Z or Embodiment AA, further comprising the step of operably connecting the apparatus or the assembly to a source of negative pressure.

Embodiment CC is the method of Embodiment BB, wherein ejecting the at least one analyte capture element comprises sliding the capture element out of an opening at the second end of the apparatus.

Embodiment DD is the method of any one of Embodiments Z through CC, wherein ejecting the at least one analyte capture element from the channel comprises moving a discharge element through a portion of the channel to eject the analyte capture element from the channel.

Embodiment EE is the method of any one of Embodiments Z through DD, wherein the at least one capture element comprises a porous medium, wherein contacting the liquid sample with the at least one capture element comprises passing the liquid sample through the porous medium.

Embodiment FF is the method of any one of Embodiments Z through EE, further comprising the step of processing the at least one analyte capture element and/or sample material associated therewith to permeabilize a cell.

Embodiment GG is the method of any one of Embodiments Z through FF, wherein detecting a presence or an absence an analyte retained from the sample comprises detecting a nucleotide, a nucleic acid, an enzyme, an antigen or a combination of any two or more of the foregoing analytes.

Embodiment HH is the method of Embodiment GG, wherein the analyte is associated with a cell of interest.

Embodiment II is the method of any one of Embodiments Z through HH, further comprising the step of coupling at least one outlet to a container, wherein ejecting the at least one analyte capture element from the channel comprises ejecting the analyte capture element into the container.

Embodiment JJ is a kit, comprising:
an apparatus comprising:
a body having a first end and a second end opposite the first end, the body comprising:
a plurality of spaced-apart reservoirs in a linear array, each reservoir comprising a sample-receiving opening proximate the first end;
a plurality of spaced-apart effluent discharge openings, each effluent discharge opening in fluid communication with one of the plurality of sample-receiving openings via a flow path;

a plurality of channels, each channel intersecting one of the flow paths;
   wherein each channel comprises a second channel opening proximate the second end;
   wherein each channel is dimensioned to receive a analyte capture element; and
a plurality of spaced-apart outlets extending from the body, each of the outlets comprising one of the second channel openings.

Embodiment KK is the kit of claim JJ, further comprising a waste receptacle;
   wherein the waste receptacle comprises a plurality of spaced-apart chambers, each chamber having an outlet-receiving opening, an interior volume, and a drain;
   wherein the plurality of spaced-apart chambers comprises:
      a first chamber having a first interior volume and a first drain;
      a second chamber adjacent the first chamber, the second chamber having a second interior volume and a second drain;
      wherein, when the apparatus and the waste receptacle are operably coupled, at least a portion of the first outlet is disposed in the first interior volume forming a first flow path extending from the first sample-receiving opening to the first drain, and at least a portion of the second outlet is disposed in the second interior volume forming a second flow path extending from the second sample-receiving opening to the second drain; and
      wherein a first shortest distance between a first outlet opening and a second outlet opening is shorter than a second shortest distance between the first drain and the second drain.

Embodiment LL is the kit of Embodiment JJ or Embodiment KK, further comprising an analyte capture element that is configured to be disposed in one of the plurality of channels such that liquid passing through one of the flow paths from the first end to the second end contacts the analyte capture element.

Embodiment MM is the kit of any one of Embodiments JJ through LL, further comprising at least one analyte capture element discharger.

Embodiment NN is the kit of any one of Embodiments JJ through MM, further comprising a reagent.

Embodiment OO is the kit of Embodiment NN, wherein the reagent comprises a cell lysis agent or a detection agent.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:
1. An assembly, comprising:
an apparatus for processing a sample, the apparatus comprising:
   a body having a first end and a second end opposite the first end, the body comprising:
      a plurality of spaced-apart reservoirs in a linear array, each reservoir comprising a sample-receiving opening, the plurality of reservoirs comprising a first reservoir and a second reservoir adjacent the first reservoir;
         wherein the first reservoir has a first sample-receiving opening;
      a plurality of spaced-apart effluent discharge openings, each effluent discharge opening in fluid communication with one of the plurality of sample-receiving openings via a liquid flow path, the plurality of effluent discharge openings comprising a first effluent discharge opening;
      a plurality of liquid flow paths, the plurality of liquid flow paths comprising a first liquid flow path;
         wherein the first liquid flow path extends from the first sample-receiving opening to the first effluent discharge opening;
         wherein the first effluent discharge opening is in fluid communication with the first sample-receiving opening via the first liquid flow path;
      a plurality of channels, each channel intersecting one liquid flow path of the plurality of liquid flow paths, the plurality of channels comprising a first channel;
         wherein the first channel intersects the first liquid flow path;
         wherein each channel of the plurality of channels comprises a channel exit opening proximate the second end;
         wherein the first channel comprises a first channel exit opening;
         wherein each channel of the plurality of channels is dimensioned to receive an analyte capture element; and
      a plurality of spaced-apart outlets extending from the body;
         wherein each of the outlets comprises one of the channel exit openings;
         wherein the plurality of outlets includes a first outlet;
         wherein the first outlet comprises the first channel exit opening;
      wherein the second reservoir has a second sample-receiving opening and a second outlet having a second effluent discharge opening; and
   a waste receptacle operably coupled to the apparatus;
      wherein the waste receptacle comprises a plurality of spaced-apart chambers, wherein the plurality of spaced-apart chambers comprises:
         a first chamber having a first interior volume and a first drain; and
         a second chamber adjacent the first chamber, the second chamber having a second interior volume and a second drain; and
an analyte capture element slideably engaged in one of the channels;
wherein the first liquid flow path further extends from the first sample-receiving opening to the first drain, and a second liquid flow path extends from the second sample-receiving opening to the second drain;

wherein a first shortest distance between the first effluent discharge opening and the second effluent discharge opening is shorter than a second shortest distance between the first drain and the second drain.

2. The assembly of claim 1, wherein the first outlet further comprises the first effluent discharge opening.

3. The assembly of claim 1, wherein the first effluent discharge opening and the first channel exit opening define a common opening.

4. The assembly of claim 1 wherein the analyte capture element is slideably engaged in the first channel at a location that is in fluid communication with the first liquid flow path.

5. The assembly of claim 4, wherein the apparatus further comprises a primary retention structure disposed in the first channel, wherein the primary retention structure is configured to position the analyte capture element at a location in the first channel where the analyte capture element is in fluid communication with the first liquid flow path.

6. The assembly of claim 5, further comprising a secondary retention structure disposed in the channel, wherein the first and secondary retention structures are configured to releasably hold the analyte capture element at a location where the analyte capture element is in fluid communication with the first liquid flow path.

7. The assembly of claim 4, wherein the apparatus is configured such that substantially all liquid passing through the first liquid flow path from the first sample-receiving opening to the first effluent discharge opening passes through the analyte capture element.

8. The assembly of claim 1, wherein the first channel extends from the first channel exit opening to a first channel entrance opening.

9. The assembly of claim 1, further comprising an analyte capture element discharger comprising a post, wherein a portion of the post is disposed in the first channel, wherein the discharger is configured to move through the first channel and to urge the analyte capture element out of the first channel exit opening.

10. The assembly of claim 1, further comprising a prefilter disposed in the first liquid flow path between the first sample-receiving opening and the first channel.

11. The assembly of claim 1, wherein each outlet of the plurality of outlets is shaped, dimensioned, and spaced apart such that the plurality of outlets can be received into a linear array of two or more tubes.

12. A method of detecting a presence or an absence of an analyte in a sample, the method comprising:
providing a liquid sample and an apparatus comprising,
a body having a first end and a second end opposite the first end, the body comprising:
a plurality of spaced-apart reservoirs in a linear array, each reservoir comprising a sample-receiving opening, the plurality of reservoirs comprising a first reservoir and a second reservoir adjacent the first reservoir;
wherein the first reservoir has a first sample-receiving opening;
a plurality of spaced-apart effluent discharge openings, each effluent discharge opening in fluid communication with one of the plurality of sample-receiving openings via a liquid flow path, the plurality of effluent discharge openings comprising a first effluent discharge opening;
a plurality of liquid flow paths, the plurality of liquid flow paths comprising a first liquid flow path;
wherein the first liquid flow path extends from the first sample-receiving opening to the first effluent discharge opening;
wherein the first effluent discharge opening is in fluid communication with the first sample-receiving opening via the first liquid flow path;
a plurality of channels, each channel intersecting one liquid flow path of the plurality of liquid flow paths, the plurality of channels comprising a first channel;
wherein the first channel intersects the first liquid flow path;
wherein each channel of the plurality of channels comprises a channel exit opening proximate the second end;
wherein the first channel comprises a first channel exit opening;
wherein each channel of the plurality of channels is dimensioned to receive an analyte capture element;
a plurality of spaced-apart outlets extending from the body;
wherein each of the outlets comprises one of the channel exit openings;
wherein the plurality of outlets includes a first outlet;
wherein the first outlet comprises the first channel exit opening; and an analyte capture element;
wherein the analyte capture element is movably engaged in the first channel at a location that is in fluid communication with the first liquid flow path;
contacting the liquid sample with the analyte capture element; ejecting the analyte capture element from the channel; and
detecting a presence or an absence of an analyte retained from the sample by the analyte capture element.

13. The method of claim 12, wherein contacting the liquid sample with the analyte capture element comprises loading the sample into one of the plurality of reservoirs that is in fluidic communication with the analyte capture element.

14. The method of claim 12, wherein ejecting the analyte capture element from the channel comprises moving a discharge element through a portion of the channel to eject the analyte capture element from the channel.

15. The method of claim 12, wherein the analyte capture element comprises a porous medium, wherein contacting the liquid sample with the analyte capture element comprises passing the liquid sample through the porous medium.

16. The method of claim 12, further comprising the step of coupling at least one of the plurality of outlets to a container, wherein ejecting the analyte capture element from the channel comprises ejecting the analyte capture element into the container.

17. A kit, comprising:
an apparatus comprising:
a body having a first end and a second end opposite the first end, the body comprising:
a plurality of spaced-apart reservoirs in a linear array, each reservoir comprising a sample-receiving opening proximate the first end, the plurality of reservoirs including a first reservoir with a first sample-receiving opening and a second reservoir with a second sample-receiving opening;
a plurality of spaced-apart effluent discharge openings, each effluent discharge opening in fluid communication with one of the plurality of sample-receiving openings via a liquid flow path;

a plurality of liquid flow paths, each liquid flow path extending from the sample-receiving opening of each of the plurality of reservoirs to one effluent discharge opening of the plurality of effluent discharge openings;

wherein the one of the plurality of effluent discharge openings is in fluid communication with one of the plurality of sample-receiving openings via one of the plurality of liquid flow paths;

wherein the plurality of effluent discharge openings includes a first effluent discharge opening and a second effluent discharge opening;

a plurality of channels, each channel intersecting one of the liquid flow paths;

wherein each channel comprises a channel exit opening proximate the second end;

wherein each channel is dimensioned to receive an analyte capture element;

a plurality of spaced-apart outlets extending from the body, each of the outlets comprising one of the channel exit openings; and a waste receptacle comprising a plurality of spaced-apart chambers, each chamber having an outlet-receiving opening, an interior volume, and a drain;

wherein the plurality of spaced-apart chambers comprises:

a first chamber having a first interior volume and a first drain; and a second chamber adjacent the list chamber, the second chamber having a second interior volume and a second drain;

wherein, when the apparatus and the waste receptacle are operably coupled, at least a portion of a first outlet is disposed in the first interior volume forming a first liquid flow path extending from the first sample-receiving opening to the first drain, and at least a portion of a second outlet is disposed in the second interior volume forming a second liquid flow path extending from the second sample-receiving opening to the second drain; and wherein a first shortest distance between the first effluent discharge opening and the second effluent discharge opening is shorter than a second shortest distance between the first drain and the second drain.

18. The kit of claim 17, further comprising an analyte capture element that is configured to be disposed in one of the plurality of channels.

19. The kit of claim 17, further comprising at least one analyte capture element discharger.

20. The kit of claim 17, further comprising a reagent, wherein the reagent comprises a cell lysis agent or a detection agent.

* * * * *